United States Patent
Bowman et al.

(10) Patent No.: US 9,808,599 B2
(45) Date of Patent: Nov. 7, 2017

(54) DEVICE DELIVERY SYSTEM

(71) Applicant: MicroVention, Inc., Tustin, CA (US)

(72) Inventors: Heath Bowman, Trabuco Canyon, CA (US); Ross Tsukashima, San Diego, CA (US)

(73) Assignee: MicroVention, Inc., Tustin, CA (US)

( * ) Notice: Subject to any disclaimer, the term of this patent is extended or adjusted under 35 U.S.C. 154(b) by 157 days.

(21) Appl. No.: 14/578,106

(22) Filed: Dec. 19, 2014

(65) Prior Publication Data

US 2015/0173772 A1   Jun. 25, 2015

Related U.S. Application Data

(60) Provisional application No. 61/919,669, filed on Dec. 20, 2013.

(51) Int. Cl.
*A61B 17/12* (2006.01)
*A61M 25/01* (2006.01)
*A61M 25/09* (2006.01)
*A61B 17/00* (2006.01)

(52) U.S. Cl.
CPC ..... *A61M 25/0138* (2013.01); *A61B 17/1214* (2013.01); *A61B 17/12163* (2013.01); *A61M 25/09041* (2013.01); *A61B 2017/00115* (2013.01); *A61B 2017/1209* (2013.01); *A61B 2017/12054* (2013.01); *A61B 2017/12063* (2013.01); *A61B 2017/12068* (2013.01); *A61M 25/0158* (2013.01)

(58) Field of Classification Search
CPC .......... A61B 17/12022; A61B 17/1214; A61B 2017/1205; A61B 2017/12054; A61B 2017/12059; A61B 2017/12063; A61B 2017/12068; A61B 2017/12077; A61B 2017/1209; A61M 25/01; A61M 25/06; A61M 25/09; A61M 25/09041; A61M 2025/0058; A61F 2/95; A61F 2002/11
See application file for complete search history.

(56) References Cited

U.S. PATENT DOCUMENTS

| | | | |
|---|---|---|---|
| 2,548,602 | A | 4/1951 | Greenburg |
| 3,021,834 | A | 2/1962 | Sheldon |
| 3,470,876 | A | 10/1969 | Barchilon |
| 3,726,269 | A | 4/1973 | Webster |
| 3,769,981 | A | 11/1973 | McWhorter |

(Continued)

FOREIGN PATENT DOCUMENTS

| | | |
|---|---|---|
| EP | 0830873 A2 | 3/1998 |
| EP | 0992220 A1 | 4/2000 |

(Continued)

OTHER PUBLICATIONS

WIPO, U.S. International Searching Authority, International Search Report and Written Opinion mailed Jun. 9, 2015 in International Patent Application No. PCT/US2014/071696.

*Primary Examiner* — Todd J Scherbel
(74) *Attorney, Agent, or Firm* — Inskeep IP Group, Inc.

(57) ABSTRACT

A catheter system utilizing one or more sensors is described. The catheter can be used as part of an embolic coil system, guidewire system, or combined embolic coil/guidewire system where the devices interact with the catheter system. A variable detachment embolic coil system and guidewire system are also described.

18 Claims, 38 Drawing Sheets

(56) References Cited

U.S. PATENT DOCUMENTS

| | | |
|---|---|---|
| 3,773,034 A | 11/1973 | Burns et al. |
| 4,033,331 A | 7/1977 | Guss |
| 4,141,364 A | 2/1979 | Schultze |
| 4,195,637 A | 4/1980 | Gruntzig et al. |
| 4,215,703 A | 8/1980 | Willson |
| 4,230,108 A | 10/1980 | Young |
| 4,248,234 A | 2/1981 | Assenza et al. |
| 4,498,473 A | 2/1985 | Gereg |
| 4,535,757 A | 8/1985 | Webster, Jr. |
| 4,554,928 A | 11/1985 | Webster, Jr. |
| 4,570,354 A | 2/1986 | Hindes |
| 4,573,470 A | 3/1986 | Samson et al. |
| 4,576,177 A | 3/1986 | Webster, Jr. |
| 4,582,181 A | 4/1986 | Samson |
| 4,586,923 A | 5/1986 | Gould et al. |
| 4,601,705 A | 7/1986 | McCoy |
| 4,616,652 A | 10/1986 | Simpson |
| 4,662,404 A | 5/1987 | Leveen et al. |
| 4,676,249 A | 6/1987 | Arenas et al. |
| 4,685,473 A | 8/1987 | Karcher et al. |
| 4,758,222 A | 7/1988 | McCoy |
| 4,822,345 A | 4/1989 | Danforth |
| 4,898,577 A | 2/1990 | Badger et al. |
| 4,921,482 A | 5/1990 | Hammerslag |
| 4,944,727 A | 7/1990 | McCoy |
| 4,957,481 A | 9/1990 | Gatenby |
| 4,960,134 A | 10/1990 | Webster, Jr. |
| 4,976,691 A | 12/1990 | Sahota |
| 4,989,608 A | 2/1991 | Ratner |
| 5,025,799 A | 6/1991 | Wilson |
| 5,037,391 A | 8/1991 | Hammerslag et al. |
| 5,057,092 A | 10/1991 | Webster, Jr. |
| 5,065,761 A | 11/1991 | Pell |
| 5,073,168 A | 12/1991 | Danforth |
| 5,078,714 A | 1/1992 | Katims |
| 5,090,958 A | 2/1992 | Sahota |
| 5,114,402 A | 5/1992 | McCoy |
| 5,122,115 A | 6/1992 | Marks |
| 5,122,136 A | 6/1992 | Guglielmi et al. |
| 5,143,093 A | 9/1992 | Sahota |
| 5,147,377 A | 9/1992 | Sahota |
| 5,160,321 A | 11/1992 | Sahota |
| 5,166,875 A | 11/1992 | Machida |
| 5,168,864 A | 12/1992 | Shockey |
| 5,174,297 A | 12/1992 | Daikuzono |
| 5,195,968 A | 3/1993 | Lundquist |
| 5,199,950 A | 4/1993 | Schmitt et al. |
| 5,203,776 A | 4/1993 | Durfee |
| 5,211,165 A | 5/1993 | Dumoulin et al. |
| 5,211,183 A | 5/1993 | Wilson |
| 5,217,484 A | 6/1993 | Marks |
| 5,267,960 A | 12/1993 | Hayman et al. |
| 5,267,982 A | 12/1993 | Sylvanowicz |
| 5,290,266 A | 3/1994 | Rohling et al. |
| 5,291,890 A | 3/1994 | Cline et al. |
| 5,295,484 A | 3/1994 | Marcus et al. |
| 5,295,486 A | 3/1994 | Wollschlager et al. |
| 5,306,263 A | 4/1994 | Voda |
| 5,320,605 A | 6/1994 | Sahota |
| 5,322,064 A | 6/1994 | Lundquist |
| 5,327,905 A | 7/1994 | Avitall |
| 5,328,467 A | 7/1994 | Edwards et al. |
| 5,348,536 A | 9/1994 | Young et al. |
| 5,354,295 A | 10/1994 | Guglielmi et al. |
| 5,360,441 A | 11/1994 | Otten |
| 5,368,564 A | 11/1994 | Savage |
| 5,368,592 A | 11/1994 | Stern et al. |
| 5,370,617 A | 12/1994 | Sahota |
| 5,373,849 A | 12/1994 | Maroney et al. |
| 5,383,923 A | 1/1995 | Webster, Jr. |
| 5,385,148 A | 1/1995 | Lesh et al. |
| 5,386,741 A | 2/1995 | Rennex |
| 5,389,072 A | 2/1995 | Imran |
| 5,391,199 A | 2/1995 | Ben-Haim |
| 5,401,258 A | 3/1995 | Voda |
| 5,403,291 A | 4/1995 | Abrahamson |
| 5,411,025 A | 5/1995 | Webster, Jr. |
| 5,423,321 A | 6/1995 | Fontenot |
| 5,423,882 A | 6/1995 | Jackman et al. |
| 5,431,168 A | 7/1995 | Webster, Jr. |
| 5,445,625 A | 8/1995 | Voda |
| 5,450,846 A | 9/1995 | Goldreyer |
| 5,451,206 A | 9/1995 | Young |
| 5,478,330 A | 12/1995 | Imran et al. |
| 5,487,757 A | 1/1996 | Truckai et al. |
| 5,489,278 A | 2/1996 | Abrahamson |
| 5,497,784 A | 3/1996 | Imran |
| 5,500,012 A | 3/1996 | Brucker et al. |
| 5,522,836 A | 6/1996 | Palermo |
| 5,522,873 A | 6/1996 | Jackman et al. |
| 5,531,721 A | 7/1996 | Pepin et al. |
| 5,540,680 A | 7/1996 | Guglielmi et al. |
| 5,555,883 A | 9/1996 | Avitall |
| 5,556,390 A | 9/1996 | Hicks |
| 5,558,093 A | 9/1996 | Pomeranz |
| 5,569,220 A | 10/1996 | Webster, Jr. |
| 5,569,245 A | 10/1996 | Guglielmi et al. |
| 5,588,432 A | 12/1996 | Crowley |
| 5,596,989 A | 1/1997 | Morita |
| 5,624,449 A | 4/1997 | Pham et al. |
| 5,626,136 A | 5/1997 | Webster, Jr. |
| 5,628,313 A | 5/1997 | Webster, Jr. |
| 5,647,361 A | 7/1997 | Damadian |
| 5,662,116 A | 9/1997 | Kondo et al. |
| 5,733,248 A | 3/1998 | Adams et al. |
| 5,743,905 A | 4/1998 | Eder et al. |
| 5,759,161 A | 6/1998 | Ogawa et al. |
| 5,772,590 A | 6/1998 | Webster, Jr. |
| 5,782,239 A | 7/1998 | Webster, Jr. |
| 5,797,870 A | 8/1998 | March et al. |
| 5,797,960 A | 8/1998 | Stevens |
| 5,799,661 A | 9/1998 | Boyd et al. |
| 5,800,393 A | 9/1998 | Sahota |
| 5,800,497 A | 9/1998 | Bakels et al. |
| 5,820,592 A | 10/1998 | Hammerslag |
| 5,823,956 A | 10/1998 | Roth et al. |
| 5,824,031 A | 10/1998 | Cookston et al. |
| 5,829,447 A | 11/1998 | Stevens et al. |
| 5,830,196 A | 11/1998 | Hicks |
| 5,851,206 A | 12/1998 | Guglielmi et al. |
| 5,855,578 A | 1/1999 | Guglielmi et al. |
| 5,855,614 A | 1/1999 | Stevens et al. |
| 5,860,914 A | 1/1999 | Chiba et al. |
| 5,868,700 A | 2/1999 | Voda |
| 5,885,247 A | 3/1999 | Slagboom |
| 5,885,259 A | 3/1999 | Berg |
| 5,902,287 A | 5/1999 | Martin |
| 5,904,657 A | 5/1999 | Unsworth |
| 5,941,872 A | 8/1999 | Berg |
| 5,947,962 A | 9/1999 | Guglielmi et al. |
| 5,947,963 A | 9/1999 | Guglielmi |
| 5,951,513 A | 9/1999 | Miraki |
| 5,951,514 A | 9/1999 | Sahota |
| 5,957,911 A | 9/1999 | Nesto |
| 5,976,126 A | 11/1999 | Guglielmi |
| 5,976,131 A | 11/1999 | Guglielmi et al. |
| 6,010,498 A | 1/2000 | Guglielmi |
| 6,015,402 A | 1/2000 | Sahota |
| 6,077,260 A * | 6/2000 | Wheelock ........ A61B 17/12022 606/108 |
| 6,083,170 A | 7/2000 | Ben-Haim |
| 6,083,213 A | 7/2000 | Voda |
| 6,110,163 A | 8/2000 | Voda |
| 6,120,495 A | 9/2000 | Voda |
| 6,126,631 A | 10/2000 | Loggie |
| 6,156,061 A | 12/2000 | Wallace et al. |
| 6,159,206 A | 12/2000 | Ogawa |
| 6,199,262 B1 | 3/2001 | Martin |
| 6,206,849 B1 | 3/2001 | Martin et al. |
| 6,277,126 B1 | 8/2001 | Barry et al. |
| 6,280,423 B1 | 8/2001 | Davey et al. |
| 6,346,074 B1 | 2/2002 | Roth |
| 6,348,041 B1 | 2/2002 | Klint |
| 6,368,302 B1 | 4/2002 | Fitzmaurice et al. |

(56) References Cited

U.S. PATENT DOCUMENTS

| | | |
|---|---|---|
| 6,383,146 B1 | 5/2002 | Klint |
| 6,401,720 B1 | 6/2002 | Stevens |
| 6,425,914 B1 | 7/2002 | Wallace et al. |
| 6,475,195 B1 | 11/2002 | Voda |
| 6,551,305 B2 | 4/2003 | Ferrera et al. |
| 6,558,368 B1 | 5/2003 | Voda |
| 6,589,227 B2 | 7/2003 | Sønderskov |
| 6,595,983 B2 | 7/2003 | Voda |
| 6,651,671 B1 | 11/2003 | Donlon et al. |
| 6,651,672 B2 | 11/2003 | Roth |
| 6,672,338 B1 | 1/2004 | Esashi |
| 6,679,268 B2 | 1/2004 | Stevens et al. |
| 6,733,473 B1 | 5/2004 | Reifart et al. |
| 6,743,236 B2 | 6/2004 | Barry et al. |
| 6,743,251 B1 | 6/2004 | Eder |
| 6,755,794 B2 | 6/2004 | Soukup |
| 6,776,765 B2 | 8/2004 | Soukup et al. |
| 6,955,175 B2 | 10/2005 | Stevens et al. |
| 6,966,892 B2 | 11/2005 | Gandhi et al. |
| 7,008,395 B1 | 3/2006 | Loggie |
| 7,025,758 B2 | 4/2006 | Klint |
| 7,025,768 B2 | 4/2006 | Elliott |
| 7,100,614 B2 | 9/2006 | Stevens et al. |
| 7,179,276 B2 | 2/2007 | Barry et al. |
| 7,182,774 B2 | 2/2007 | Barry et al. |
| 7,238,194 B2 | 7/2007 | Monstadt et al. |
| 7,291,127 B2 | 11/2007 | Eidenschink |
| 7,300,458 B2 | 11/2007 | Henkes et al. |
| 7,485,122 B2 | 2/2009 | Teoh |
| 7,651,513 B2 | 1/2010 | Teoh et al. |
| 7,682,352 B2 | 3/2010 | Rafiee et al. |
| 7,722,637 B2 | 5/2010 | Barry et al. |
| 7,736,323 B2 | 6/2010 | Von Weymarn-Scharli |
| 7,749,266 B2 | 7/2010 | Forster et al. |
| 7,785,341 B2 | 8/2010 | Forster et al. |
| 7,867,218 B1 | 1/2011 | Voda |
| 7,892,186 B2 | 2/2011 | Soukup et al. |
| 7,892,231 B2 | 2/2011 | Elliott |
| 7,901,704 B2 | 3/2011 | Richard |
| 7,938,845 B2 | 5/2011 | Aganon et al. |
| 7,951,206 B2 | 5/2011 | St. Pierre |
| 7,998,132 B2 | 8/2011 | Gregorich et al. |
| 8,029,457 B2 | 10/2011 | Ash et al. |
| 8,057,396 B2 | 11/2011 | Forster et al. |
| 8,128,692 B2 | 3/2012 | Forster et al. |
| 8,142,492 B2 | 3/2012 | Forster et al. |
| RE43,311 E | 4/2012 | Wallace et al. |
| 8,147,541 B2 | 4/2012 | Forster et al. |
| 8,182,506 B2 | 5/2012 | Fitz et al. |
| 8,192,480 B2 | 6/2012 | Tieu et al. |
| 8,202,292 B2 | 6/2012 | Kellett |
| 8,216,229 B2 | 7/2012 | Elliott |
| 8,221,483 B2 | 7/2012 | Ford et al. |
| 8,298,160 B2 | 10/2012 | Oslund et al. |
| 8,303,570 B2 | 11/2012 | Gregorich et al. |
| 8,328,841 B2 | 12/2012 | Levy |
| 8,376,865 B2 | 2/2013 | Forster et al. |
| 8,398,671 B2 | 3/2013 | Chen et al. |
| 8,403,981 B2 | 3/2013 | Forster et al. |
| 8,430,925 B2 | 4/2013 | Forster et al. |
| 8,460,332 B2 | 6/2013 | Tieu et al. |
| 8,500,799 B2 | 8/2013 | Forster et al. |
| 8,551,019 B1 | 10/2013 | Kroll |
| 8,585,594 B2 | 11/2013 | Forster et al. |
| 8,597,323 B1 | 12/2013 | Plaza et al. |
| 8,608,770 B2 | 12/2013 | Forster et al. |
| 8,721,625 B2 | 5/2014 | Klint |
| 8,728,156 B2 | 5/2014 | Forster et al. |
| 8,814,848 B2 | 8/2014 | Gregorich et al. |
| 8,845,676 B2 | 9/2014 | Monstadt et al. |
| 8,876,855 B2 | 11/2014 | Plaza et al. |
| 8,906,057 B2 | 12/2014 | Connor et al. |
| 8,932,317 B2 | 1/2015 | Marks et al. |
| 8,932,318 B2 | 1/2015 | Lorenzo |
| 8,940,011 B2 | 1/2015 | Teoh et al. |
| 8,945,024 B2 | 2/2015 | Takata et al. |
| 2001/0009996 A1 | 7/2001 | Ferrera |
| 2001/0056281 A1 | 12/2001 | Wallace et al. |
| 2002/0087177 A1 | 7/2002 | Wallace et al. |
| 2002/0133092 A1 | 9/2002 | Oslund et al. |
| 2003/0045921 A1 | 3/2003 | Dadd et al. |
| 2003/0097080 A1 | 5/2003 | Esashi |
| 2004/0002732 A1 | 1/2004 | Teoh et al. |
| 2004/0054322 A1 | 3/2004 | Vargas |
| 2004/0078050 A1 | 4/2004 | Monstadt et al. |
| 2005/0027244 A1 | 2/2005 | Eidenschink |
| 2005/0283183 A1 | 12/2005 | Tran |
| 2007/0083226 A1 | 4/2007 | Buiser et al. |
| 2007/0249924 A1 | 10/2007 | Takata et al. |
| 2008/0027482 A1 | 1/2008 | Sekido et al. |
| 2009/0082852 A1 | 3/2009 | Bolduc et al. |
| 2010/0076479 A1 | 3/2010 | Monstadt |
| 2010/0137898 A1 | 6/2010 | Teoh |
| 2011/0166588 A1 | 7/2011 | Connor |
| 2011/0245862 A1 | 10/2011 | Dieck et al. |
| 2012/0046687 A1 | 2/2012 | Trommeter |
| 2012/0078343 A1 | 3/2012 | Fish |
| 2012/0283812 A1 | 11/2012 | Lagodzki et al. |
| 2013/0261656 A1 | 10/2013 | Lorenzo |
| 2014/0163604 A1 | 6/2014 | Monstadt |
| 2014/0277097 A1 | 9/2014 | Kim et al. |

FOREIGN PATENT DOCUMENTS

| | | |
|---|---|---|
| EP | 1120088 A1 | 8/2001 |
| EP | 1806104 A1 | 7/2007 |
| EP | 1992308 A2 | 11/2008 |
| EP | 2695638 A2 | 2/2014 |
| WO | WO 2000/054832 A1 | 9/2000 |
| WO | WO2005060606 A2 | 7/2005 |

* cited by examiner

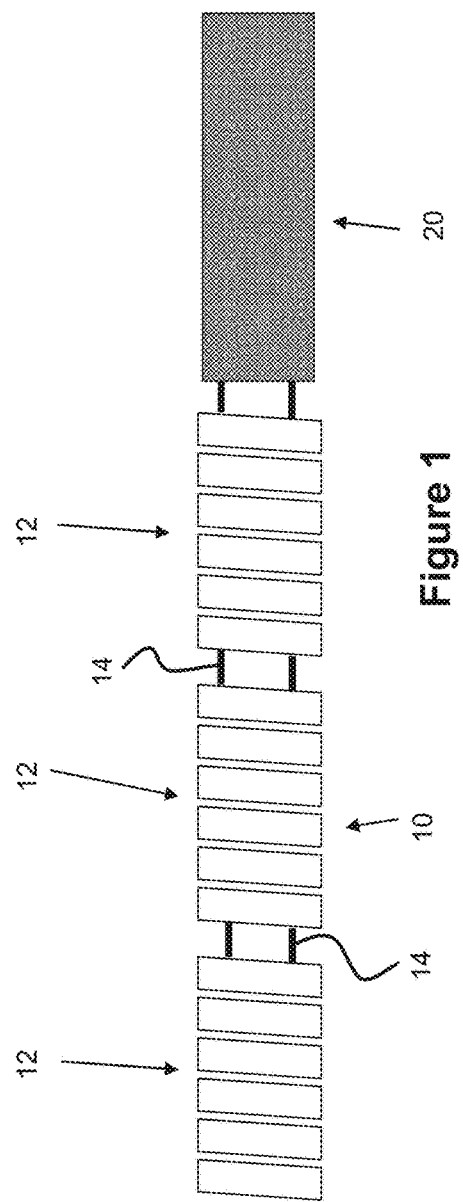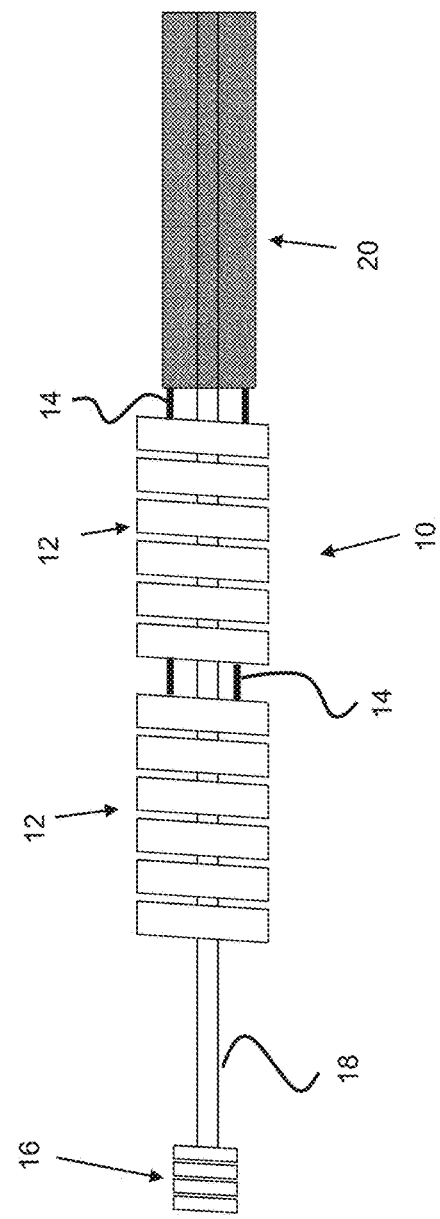

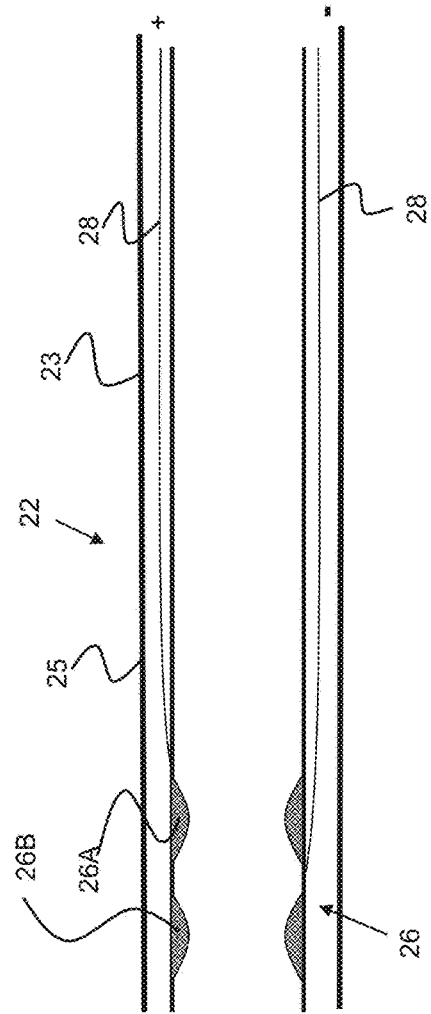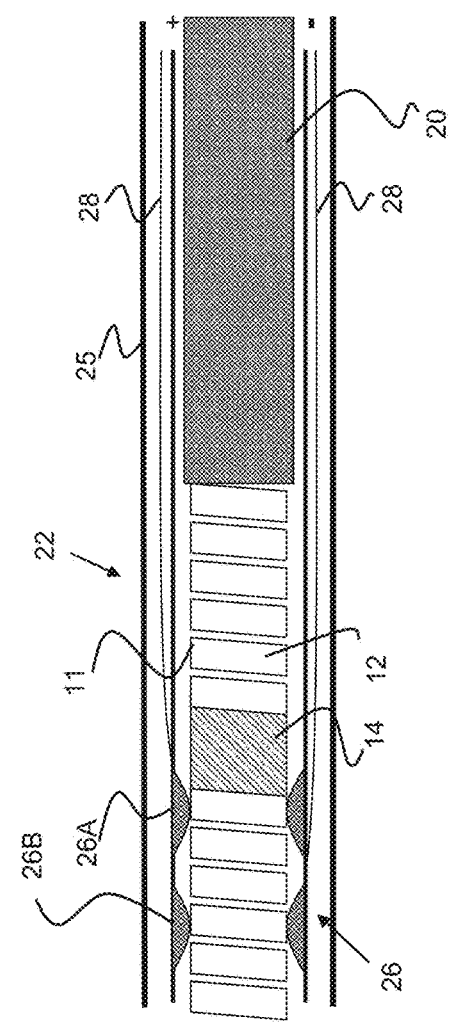

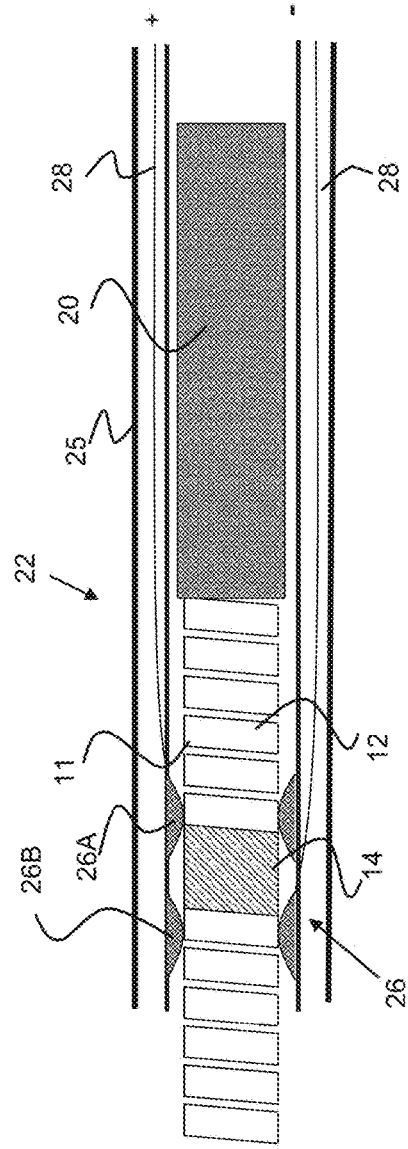
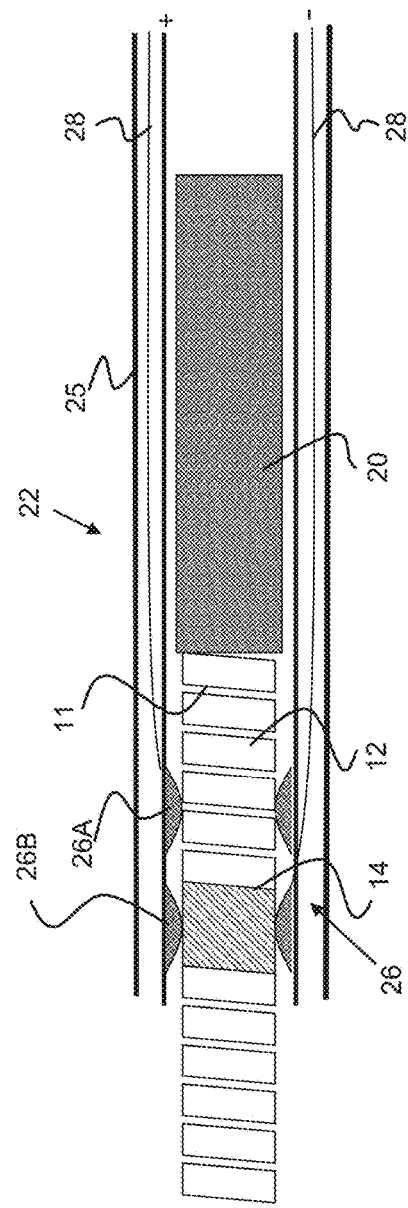

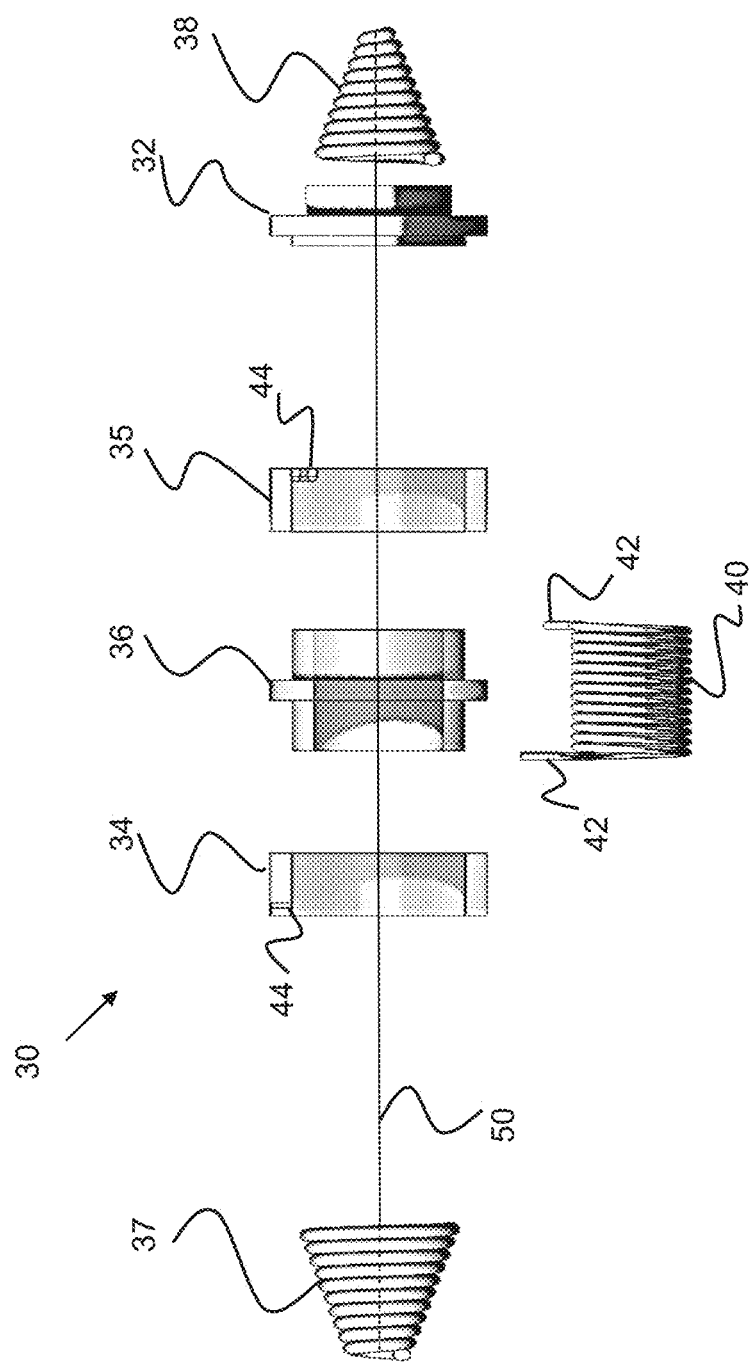

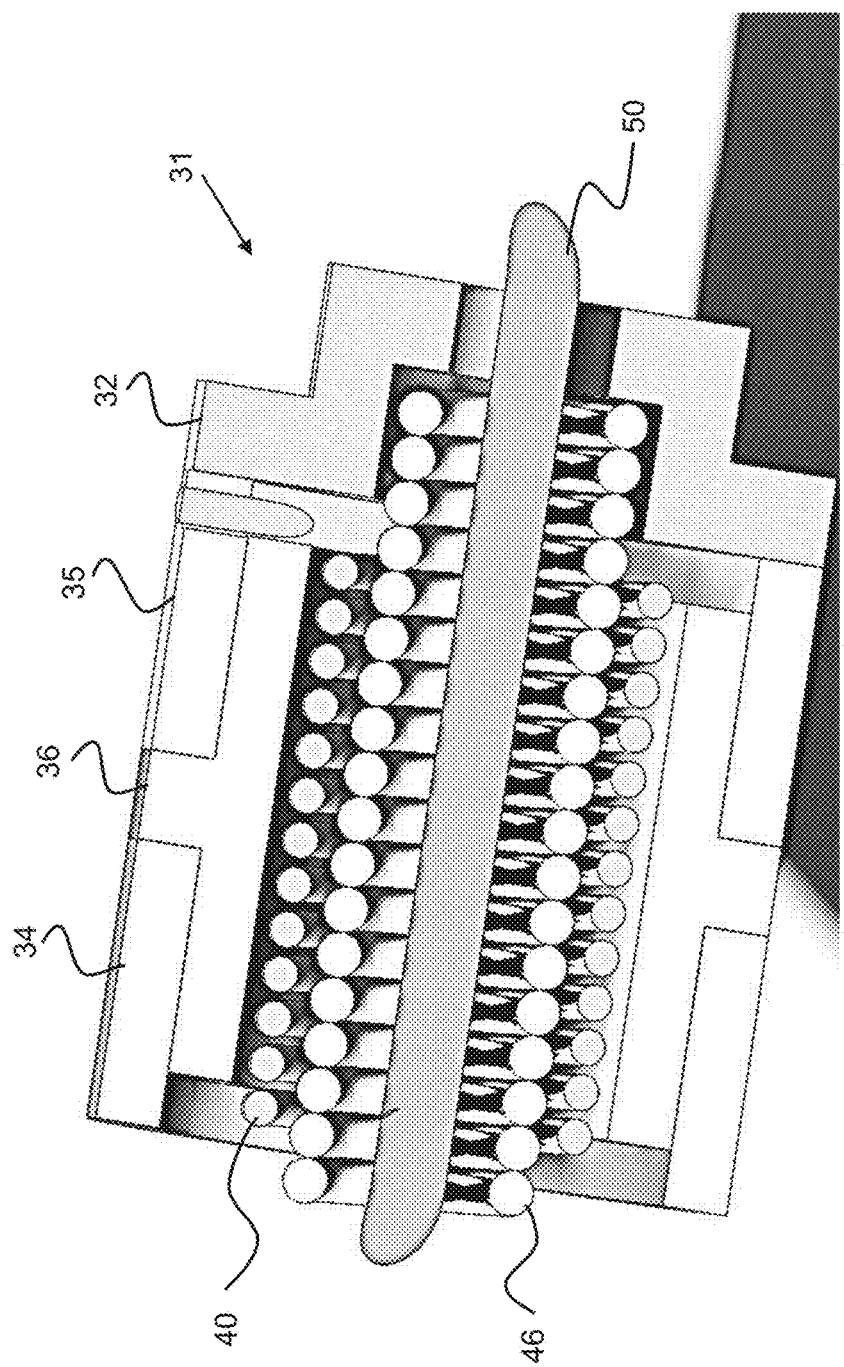

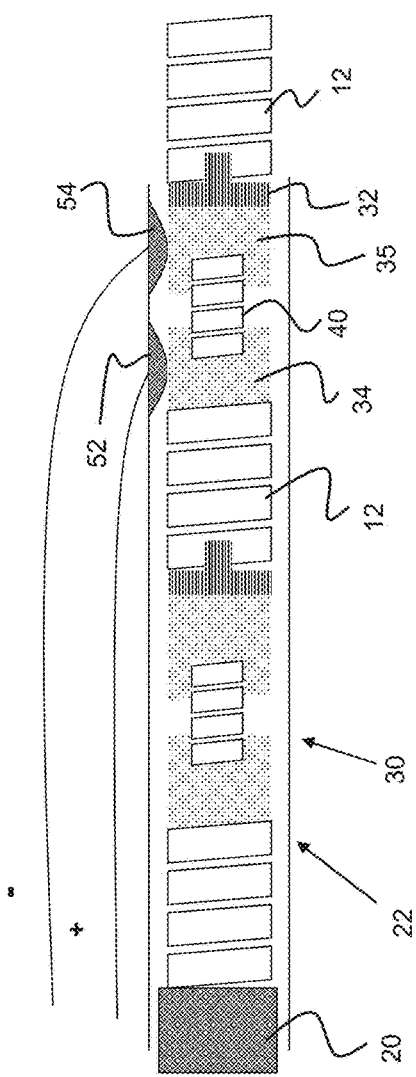
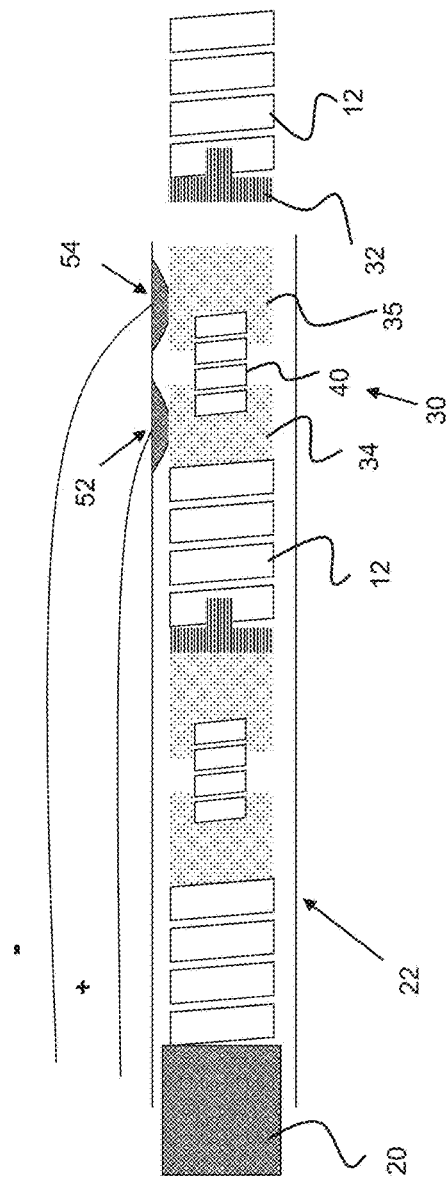

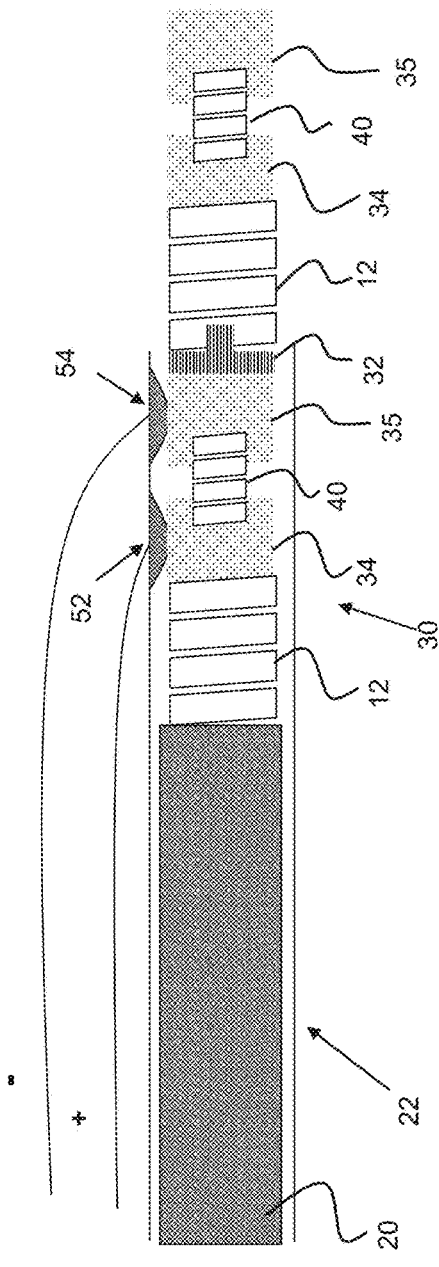
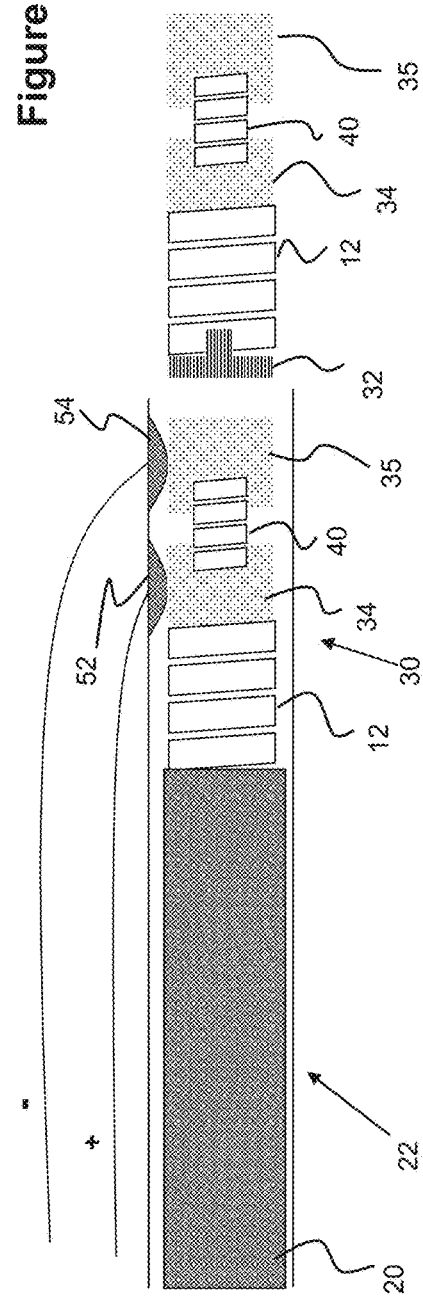

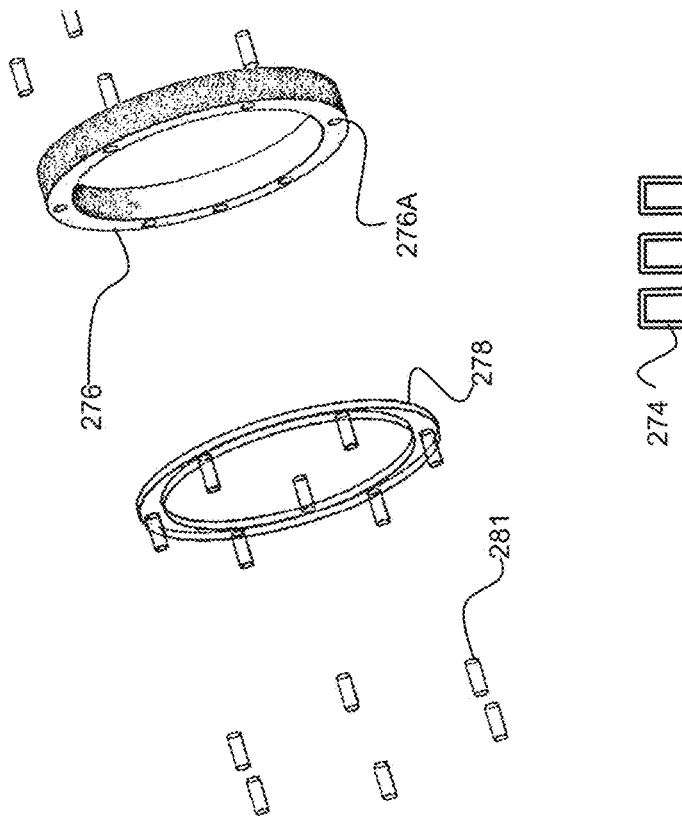
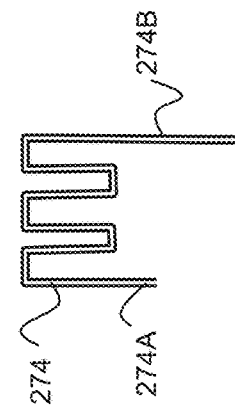
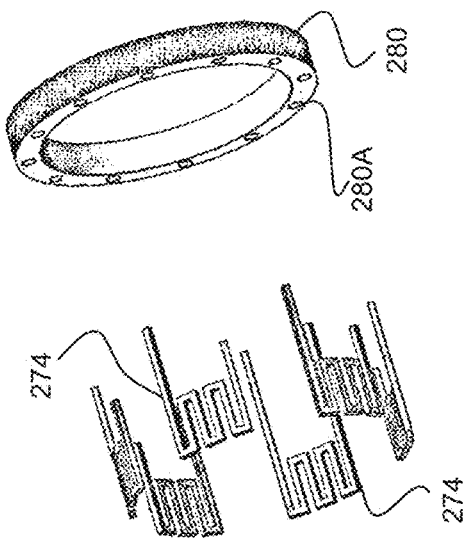
Figure 44
Figure 45

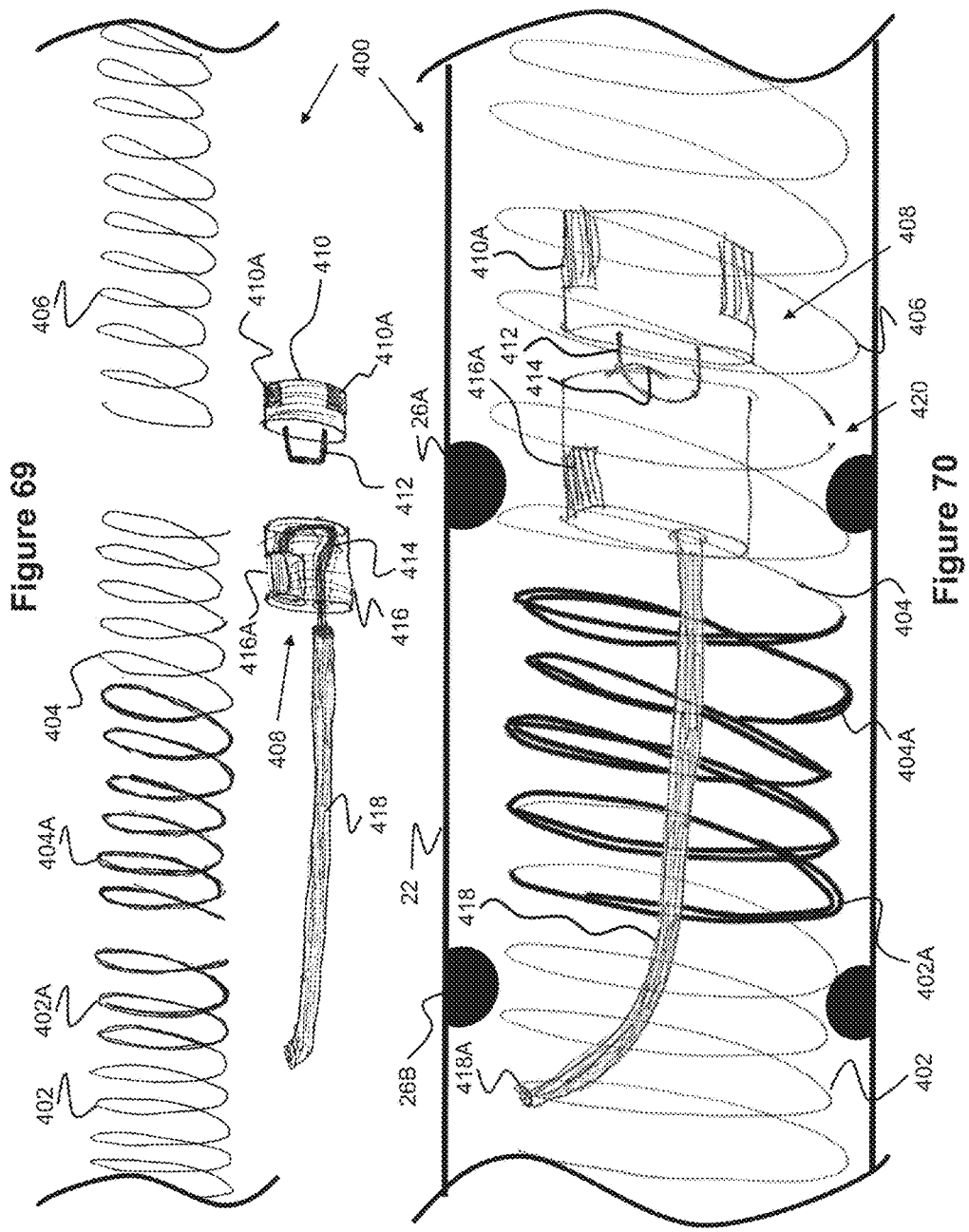

DEVICE DELIVERY SYSTEM

RELATED APPLICATIONS

This application claims priority to U.S. Provisional Application Ser. No. 61/919,669 filed Dec. 20, 2013 entitled Device Delivery System, which is hereby incorporated herein by reference in its entirety.

BACKGROUND OF THE INVENTION

Vessel occlusion is often necessary in a variety of cases including but not limited to treatment of aneurysms, atrial septal defects, patent foramen ovale, left atrial appendage occlusion, patent ductus arteriosis, fistula, arterio-venous malformations, fallopian tube occlusion for the purposes of sterilization, and occlusion in the peripheral vasculature. One method of vessel occlusion involves filling the vessel or malformation or aneurysm with coils for the purposes of embolization. Such coils may be called embolic coils. Typical embolic coil technologies utilize a set length of coil so the coils may be introduced in various stages. If the coil is too short to sufficiently pack the vessel/malformation/aneurysm multiple coils may need to be introduced, which can lengthen procedure time. If the coil is too long for the space there is a danger of the coil protruding out of the vessel/malformation/aneurysm. The use of a variable length detachable coil would allow a precise amount of embolic coil to be placed within the vessel/malformation/aneurysm.

Guidewires are typically used to track a delivery device to a particular target area within the vasculature. Navigation through tortuous anatomy can be difficult. A guidewire that could manipulate its shape within the vasculature to aid in navigation and tracking would thus be beneficial.

A catheter sensor system may be used to interact with an embolic coil in order to detach the embolic coil at one or more points along the coil. The catheter sensor system may also be used with other devices such as a guidewire. The guidewire may bend in response to an impulse conveyed via electrical contact with the one or more catheter sensors.

SUMMARY OF THE INVENTION

In one embodiment an embolic coil detachment system comprises a heater and an embolic coil with degradable links between segments of the embolic coil.

In another embodiment an embolic coil detachment system comprises a catheter with electrical contacts and an embolic coil with degradable links between segments of the embolic coil.

In another embodiment an embolic coil detachment system comprises a catheter with electrical contacts and an embolic coil with detachable links between segments of the embolic coil.

In one embodiment an embolic coil includes degradable links between segments of the embolic coil.

In another embodiment an embolic coil includes detachable links between segments of the embolic coil. The detachable links may include a degradable portion.

In another embodiment an embolic coil includes coil segments comprising the same type of coil.

In another embodiment an embolic coil includes coil segments comprising various types of coil.

In another embodiment a guidewire steering system comprises a bimetallic guidewire and a catheter with electrical contacts.

In another embodiment a guidewire steering system comprises a bimetallic guidewire and heater coil.

In another embodiment a combined embolic coil detachment and guidewire steering system comprises a catheter with electric contacts used to interface with an embolic coil and/or guidewire.

In another embodiment a microcatheter includes electrical contacts which interact with devices placed through the microcatheter.

In another embodiment, an embolic chain comprises a plurality of spheres fixed on a monofilament. The spheres can include a hollow lumen filed with a material such as a drug that can be distributed through an aperture to the lumen. The embolic chain can be detached by applying electric current (e.g., from contact within a catheter) between two adjacent spheres, causing the spheres to heat and thereby breaking the monofilament.

In another embodiment, an embolic coil is in electric communication with one terminal of a power supply and a contact on a catheter is in electric communication with another terminal of a power supply. When the catheter's contact aligns with a joint on the embolic coil and the power supply is activated, the joint breaks, releasing a portion of the embolic coil.

In another embodiment, an embolic coil is in electric communication with one terminal of a power supply and a contact on a catheter is in electric communication with another terminal of a power supply. When the power supply is activated, an electrolytically severable joint positioned outside of the catheter is degraded, severing the embolic coil. The catheter is further filled with a non-conducting fluid to prevent any joints still within the catheter from also degrading.

In another embodiment, a catheter includes a heating coil formed by laser cutting a metal hypotube or a thin, flat, metal sheet. Several heating coils can be arranged in overlapping layers within each other, axially in series along the catheter's length, or in parallel, adjacent to each other.

BRIEF DESCRIPTION OF THE DRAWINGS

FIG. 1 illustrates an embolic coil used in an embolic coil detachment system.

FIG. 2 illustrates an embolic coil detachment system utilizing the embolic coil of FIG. 1.

FIGS. 4-7 illustrate an embolic coil detachment system utilizing the embolic coil of FIG. 3.

FIGS. 9-12 illustrate an embolic coil utilizing a detachable link used in an embolic coil detachment system.

FIGS. 13-16 illustrate an embolic coil detachment system utilizing the embolic coil of FIGS. 9-12.

FIGS. 42-45 illustrates various components of the detachment system of the embolic device of FIG. 9.

FIGS. 69-70 illustrate another embodiment of an embolic device having a detachable joint.

DESCRIPTION OF EMBODIMENTS

Figure 2A:
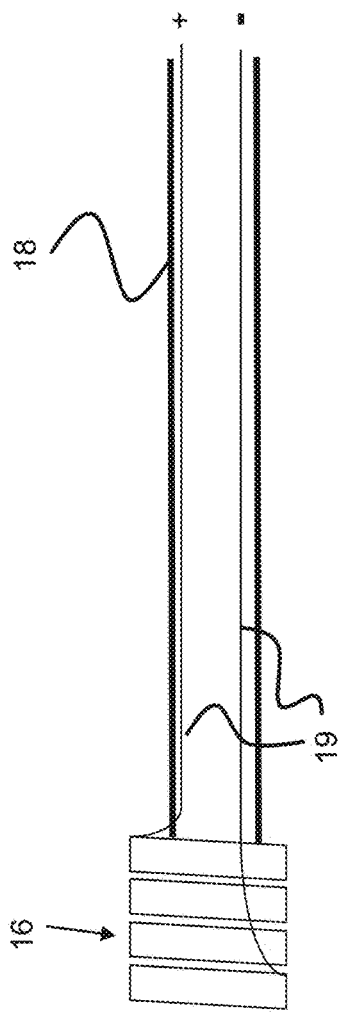
FIG. 2a shows the heater of the embolic coil detachment system of FIG. 2.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

U.S. Pat. No. 8,182,506 and US20060200192, which describe a detachment system, are hereby incorporated by reference in their entirety. The user interface described later may utilize the principles mentioned in these references.

Please note with respect to FIGS. 1-8 elements on the left side of the drawings are considered distal relative to the elements on the right side of the drawings (and, consequently, elements on the right side of the drawings are considered proximal relative to the elements on the left side of the drawings).

An embolic coil detachment system includes an embolic coil and a detachment system. FIG. 1 illustrates a coil 10 used in an embolic coil detachment system. The coil 10 includes a plurality of coil segments 12 separated by links 14 between the segments. The links 14 are degradable and, when the links are degraded sufficiently, the coil segment 12 detaches from the rest of coil 10.

A proximal pusher 20 (e.g., an elongated member attached to the coil 10 so as to push the coil 10 out of a catheter) is connected to a proximal end of the coil 10 and may optionally include another link 14 between the proximal-most coil segment and the pusher. In one example, the links 14 of FIG. 1 are thermolytically degradable. Links 14 may be made of a material which has a lower melting point than the material comprising the coil. In one example, a polymer is used for links 14. Though links 14 are shown as being a plurality of strands, a thicker solid link (such as that shown in link 14 of FIG. 3), a single strand, or a tubular member may also be used.

FIG. 2 illustrates a detachment system that can be used with the embolic coil 10 of FIG. 1. The detachment system includes a heater 16 which is located at a distal end of wire track member 18, which is preferably sized to locate the heater 16 near a distal end of a catheter. As previously discussed, the heater 16 can melt or degrade the links 14 to cause detachment between two of the various coil segments 12 from coil 10.

A proximal portion of the wire track member 18 can be located within a passage through pusher 20, thus allowing one to push or pull pusher 20 independently of any movement of wire track member 18. The material for the wire track member 18 could be any variety of metal or polymer including but not limited to stainless steel, nitinol, polyethylene, polyimide, or any combination of such materials. The wire track member 18 preferably includes negative and positive electrical current lines 19 to transfer current to the heater 16. The proximal end of the wire track member 18 can be connected to a battery or voltage source with a positive and negative terminal and a mechanism to selectively activate the power supply.

Heater 16 can be a wire coil and is preferably made of a high electrical resistive material, such as platinum or tantalum. The outer diameter of wire track member 18 and heater 16 are preferably small enough to allow the inner diameter of coil 10 to slide there over, while still fitting within a typical microcatheter. For example, for a microcatheter with a lumen that is about 0.017", the maximum outer diameter of the coil 10 may be about 0.016". Assuming a relatively large filar diameter of 0.003", the wire track member 18 may have an outer diameter less than or equal to about 0.008". The optimal size of the wire track may be as large as possible while not sacrificing the flexibility of the system. In one example, the wire track member 18 could range from 0.003" to 0.012" in outer diameter.

FIG. 2a shows a closer view of the heater 16 and wire track member 18. One of the current lines 19 connects to the proximal part of the heater 16 and another current line 19 connects to the distal part of the heater 16 to provide an outgoing and incoming flow path for the current. In this respect, the current can be selectively applied to the heater 16, generating heat. When the heater 16 is aligned with one of the links 14 of the coil 10, the heater 16 heats the link 14 from an inside of the coil 10, causing the two adjacent coil segments 12 to disconnect from each other.

The coil 10 comprising the coil segments may be made of a radiopaque biocompatible material. In one example it is made from 92/8 ratio platinum/tungsten material. For the coil shown in FIG. 1, the coil segments 12 may be connected with links 14 where the links are a monofilament made of a material such as PET (polyethylene terephthalate), Engage polymer, or PTFE (polytetrafluoroethylene). These monofilament junctions become severed by the heat generated by heater 16 when the junction is aligned correctly with the heater and when the appropriate energy is supplied to the heater. Alternatively, the links may have a tubular form where the heat generated from the heater 16 melts the linkages. In another alternate embodiment, the links 14 can be completely solid (i.e., a filled, cylindrical shape) as seen in FIG. 3.

Pusher 20 may be comprised of a hypotube of similar dimensions to the coil 10 to allow easy tracking over the wire track 18 and easy tracking within the delivery device (e.g., microcatheter). The pusher 20 can be made of a metal such as stainless steel or Nitinol, or a polymer such as polyethylene or polyimide.

Figure 3:
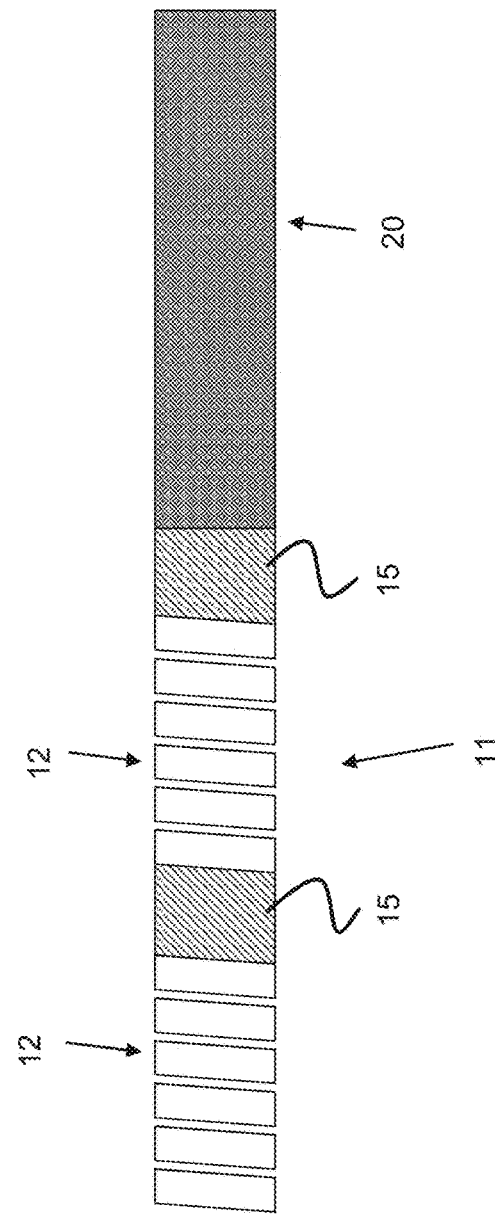
FIG. 3 illustrates another embolic coil used in an embolic coil detachment system.

FIG. 3 illustrates another coil 11 which can be used in another detachment system. The solid links 15 are shown as being thicker than the monofilament links 14 shown in FIG. 1. The coil links 15 may be interchangeable with the links 14 (i.e. both of the links shown in FIG. 1 and FIG. 3 can be used on a single coil 10, 11) depending on the properties of the coil detachment system. The figures are shown as representations of the coil embodiments and coil detachment system embodiments. Since the links 14 are preferably completely solid (or alternately cylindrical with a hollow passage), it may not be desirable to use them with the wire track member 18 and heater 16 of FIG. 2a. Therefore, it may be desirable to use a heating mechanism via a microcatheter disposed over the coil 11.

FIG. 4 illustrates a microcatheter 22 used in a coil detachment system to check or determine alignment of the embolic coil 11. The detachment system includes a microcatheter 22 with electrical contacts 26 near the distal end of the catheter 22. In FIG. 4 these contacts are shown as a pair of current carrying elements made of any electrically conductive material (one at a more proximal and one at a more distal location). Each of these contacts 26 can be rings extending around the interior circumference of the catheter's inner passage or can be one or more points or arcs that only contact a small portion of the coil 11. Other electrical contacts (a heater coil, electrodes, etc.) can also be used.

The detachment system may be used to not only check the alignment of the embolic coil 11, but initiate a detachment operation if the alignment is correct. For example, the alignment may be determined by measuring a value such as resistance, capacitance, resonant frequency, and/or metal detection between the proximal contact 26A and the distal contact 26. The contacts 26 are connected to a control system at the proximal end of the device via wires 28. The wires 28 extend between the proximal set of contacts 26A to the control system, and the distal set of contacts 26B, back to the control system. The control system can measure the correct alignment (discussed further below), as well as initiate a detachment sequence (i.e. heating to sever the linkage).

FIGS. 5-7 show the catheter 25 of FIG. 4 used to check the appropriate alignment of the embolic coil 26. Since the embolic coil 10 is composed of a series of segments 12 interconnected by links 14, the axial alignment is determined based on the measured values (e.g., resistance) between the two sets of electrical contacts 26.

For example, in FIG. 5, only one portion of the coil segment 12 contacts both the proximal contact 26A and distal contact 26B, allowing measurement of a first resistance value based on the material properties of the coil segment 12. In FIG. 6, linkage 14 contacts the distal contact 26B, while segment 12 contacts the proximal contact 26A, and therefore a second resistance value is measured based on the material properties of link 14. In FIG. 7, the distal contact 26B contacts the linkage 14 and the proximal contact 26A contacts the segment 12, therefore providing a third resistance measurement.

In one example, the desired axial alignment within the catheter 25 is shown in FIG. 6 (e.g., detected by the second resistance value), where degradation of link 14 could be initiated to separate the coil segment 12 from the rest of the coil 11. In one example, when desired alignment is measured, a signal could be relayed to the user (i.e. a light and/or sound on a user interface device). The user could interact with the interface (e.g., press a button) to initiate detachment.

In one example, contacts 26 can also relay heat to sever link 14 when desired. In another example, an alternate heat system (e.g., a heater coil within the catheter 25) coupled to the control system can be used to sever link 14 when desired. Once the user presses the button, detachment is automatically initiated once the proper resistance valued is measured based on the position of the embolic coil 11 relative to the contacts 26. In addition to thermolytic detachment, electrolytic or other detachment mechanism could also be used to sever link 14.

Contacts 26, in addition to measuring a value (e.g., resistance) to check the proper alignment of the coil components, can also transmit or cause heat to initiate detachment via degradation of links 14. For example, the contacts 26 can supply sufficient current to heat up two segments 12 on each side of a link 14, causing the segments 12 melt the link 14. Specifically, the circuit extends between the control system, through one wire 28, through one set of contacts 26, through a portion of the embolic coil (that portion which contacts between the two wires), through the other set of contacts 26, through the other wire 28, and back to the control system. One of the wires 28 can be attached to a positive terminal in a voltage source in the control system, whereas the other wire 28 can be attached to a negative terminal of the voltage source in the control system to complete the circuit. In another embodiment, each of the contacts can be connected to additional wires that selectively cause each of the contacts to themselves generate heat.

Figure 8:
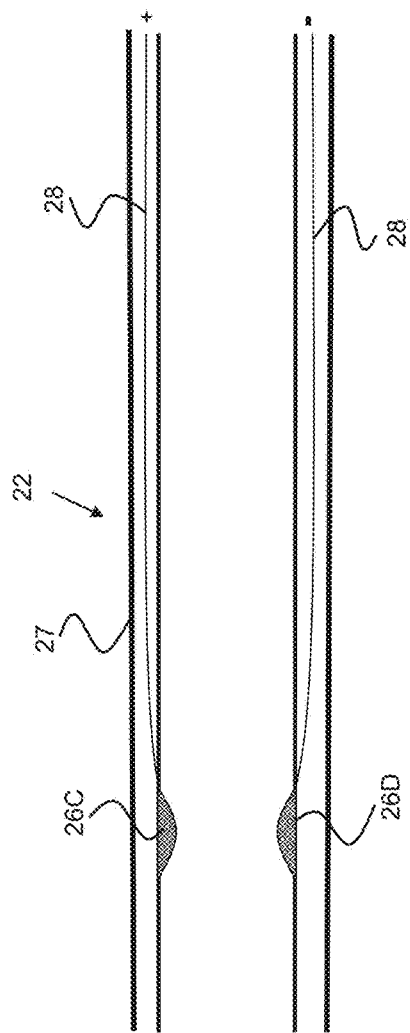
FIG. 8 illustrate another embolic coil detachment system utilizing the embolic coil of FIG. 3.

FIG. 8 illustrates a catheter 27 similar to the catheter 25 shown in FIG. 4, except the contacts 26C and 26D comprise a parallel plate capacitor. Specifically, contact 26C and 26D are each a plate, arc, circular point shape or similar shape, and are preferably located immediately across from each other within the lumen of the catheter 27. The contacts 26C and 26D are coupled via wires 28 to positive and negative terminals of a control system similar to the one described earlier, allowing capacitance to be measured. Depending on the dielectric constant of the material passing between the parallel contacts 26C and 26D, the capacitance will vary. Thus one capacitance value will be observed for the coil segment 12, while another dielectric constant value will be observed for the link 14, since they are made of different materials. When a particular capacitance value is measured by the control system based on the measured dielectric constant of link 14, a detachment sequence similar to the one described earlier can be initiated.

Please note with respect to FIGS. 9-16 elements on the right side of the drawings are considered distal relative to the elements on the left side of the drawings (and, consequently, elements on the left side of the drawings are considered proximal relative to the elements on the right side of the drawings).

Figure 9:
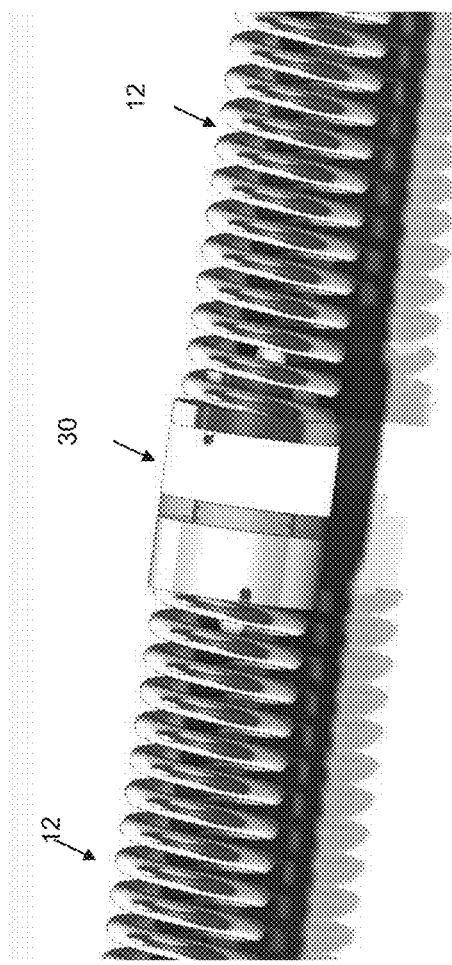

FIG. 9 illustrates a detachment system utilizing a detachable link 30 that connects two adjacent coil segments 12. The detachable link 30 comprises a capsule-like portion containing a degradable element.

Figure 10:
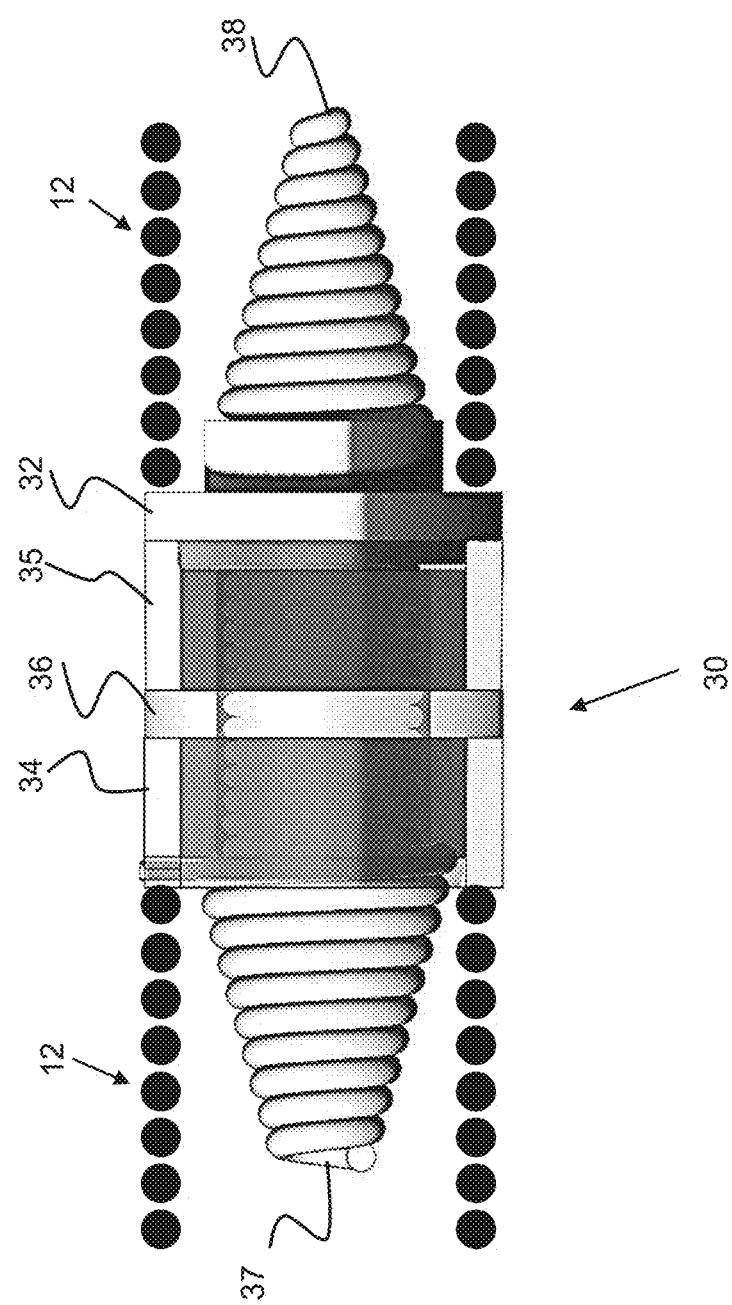

FIG. 10 shows a closer view of link 30, while FIG. 11 offers an exploded view of the link 30 shown in FIG. 10. Link 30 includes an insulating sleeve 36 which can be made of any biocompatible non-conductive material. Polymer, such as polyimide, or a ceramic are examples of materials that can be used for the insulating sleeve.

Two conductive cylinders or sleeves 34 and 35 are mated respectively to the proximal and distal ends of insulating sleeve 36 via adhesive or glue. The conductive sleeves 34, 35 are composed of a conductive material, such as a 92/8 ratio platinum/tungsten material.

Heater 40, which can be a coil of wire, spans the area between the proximal and distal conductive sleeves 34, 35, connecting its ends 42 (e.g., ends of its wire or a flared coil portion) to grooves or recesses 44 in each of the sleeves 34 and 35. Since the sleeves 34, 35 are conductive, the current can pass between the two conductive sleeves 34. 35 and through heater 40, causing the heater 40 generate heat. In one example, heater 40 is positioned over insulating sleeve 36 and in another example, heater 40 is located within insulating sleeve 36. In both examples the heater 40 would preferably not have significant contact with the insulating sleeve 36 so as to not dissipate the heat that can build up within heater 40. The heater is preferably made of a biocompatible material which also has high electrical resistance. In one example the heater is made of a 92/8 ratio platinum/tungsten material and is a coil.

Cap 32 is located distal of distal conductive sleeve 35 and is affixed to a distally located coil segment 12. In one example, the cap 32 may also be made of a 92/8 ratio platinum/tungsten material. Another embolic coil segment 12 is affixed proximal to the proximal conductive sleeve 34, and, in one example, the distal coil segment is welded to the cap 32 and the proximal coil segment is welded to the proximal conductive sleeve 34.

Spring 38 is located distal of cap 32, while another spring 37 is located proximal to the proximal conductive sleeve 34 to provide flexible connection points for a monofilament 50. The monofilament wire 50, which can be composed of a polymer (e.g., PTFE or Engage), preferably tied to a proximal part of the proximal spring 37 and a distal part of the distal spring 38, though any type of connection can be used. Preferably there is minimal slack or even some tension in the monofilament 50 when it is tied between the two springs 37, 38.

FIG. 12 shows another embodiment of a detachable link 31 used in a coil detachment system, which is similar to that discussed with regard to FIGS. 10-11, but includes a single spring 46 instead of two springs. Spring 46 spans the entire link 31 and is locate within the heater 40. Instead of the monofilament 50 spanning between the two springs, it extends within and through spring 46. In one example, the monofilament may be tied to a proximal part of spring 46 and the distal coil segment (which connects to distal cap 32). In another example, spring 46 is located externally of the heater 40.

The detachment operations utilizing link 30 or 31 will now be explained. Link 30 (or 31) sits between each embolic coil segment 12. FIG. 13 shows the embolic coil comprised of various embolic coil segments 12 and links 31 (though link 30 could also be used) between said segments. The number of segments 12 and links 31 shown in the figures are for illustrative purposes only. The links 30 include proximal conductive sleeve 34, distal conductive sleeve 35, and heater 40—among other components. The coil is delivered through a microcatheter or delivery device 22.

The delivery device includes contacts 52 and 54, similar to the previously described contacts. The contacts are connected to a control system to polarize the contacts via the wires shown; one contact has a positive polarity and the other has a negative polarity. The contacts may be connected to a control system with a voltage source where one contact is connected to the positive terminal of the voltage source and the other connected to the negative terminal of the voltage source. Alternatively, other voltage sources such as an alternating-current system can be used. As an example, contact 52 has a positive polarity and contact 54 has a negative polarity.

As seen in FIG. 13, when contact 52 aligns with proximal conductive sleeve 34 and contact 54 aligns with distal conductive sleeve 34, the circuit is completed, allowing the current to flow through positive contact 52, through proximal conductive sleeve 34, through heater coil 40, through distal conductive sleeve 35, through contact 54 and back to the control system/voltage source. In one example a user interface may house the control system/voltage source that interfaces with the system described. A visual or audio cue (i.e. a light and/or sound) can be provided when proper alignment between contacts 52, 54 and conductive sleeves 34, 35 is achieved. The user may then depress a button to initiate detachment, depressing the button provides an impulse to the system.

Heater 40 will heat up as current flows through it. Referring to FIG. 11, this heat will initially cause the monofilament wire 50 to stretch, in turn increasing tension between springs 37 and 38. When the springs 37, 38 and the filament 50 reach a sufficient tension, wire 50 will break, resulting in distal cap 32 and distal coil 38 detaching into the vasculature, as seen in FIG. 14. Note, the distal cap 32 is preferably mechanically affixed (e.g., via adhesive) to the distal conductive sleeve 35 to prevent it from detaching into the vasculature on its own. The components proximal to the cap 32 and distal coil (i.e. conductive sleeves 34 and 35, insulating sleeve 36) remain affixed with the remaining proximal embolic coil segments due to the bonding components placed between all the proximal link components, as described earlier.

If another detachment sequence is initiated at another location of the embolic coil, these other components (i.e. distal conductive sleeve 35, insulating sleeve 36, proximal conductive sleeve 34, etc.) will then detach into the vasculature when the next detachment sequence initiates. This sequence is illustrated in FIGS. 13-16. In FIG. 13, the first detachment sequence is initiated, thus separating distal cap 32 and the distal coil segment 12 from the rest of the coil as shown in FIG. 14. In FIG. 15 the coil is pushed until the next detachment zone or link 31 is lined up with the contacts 52, 54. The detachment sequence is then initiated again and the next grouping is then detached as shown in FIG. 16.

Preferably, all the link components are biocompatible, either being comprised of polymers (monofilament 50, insulating sleeve 36) or a biocompatible metal (heater 42, conductive sleeves 35 and 35, springs 37 and 38, cap 32, coil segment 12). For the link embodiment 31 shown in FIG. 12, the heat generated from heater 40 causes the monofilament wire 50 to expand and causes the unitary spring 46 which the wire is housed in to stretch until said wire breaks. Where the distal end of monofilament 50 is attached to the distal embolic coil segment 12, the distal embolic coil segment 12 will then detach.

In another embodiment, another system can be utilized to energize heater 40. This system can be coupled with the same user interface. This parallel system could utilize another set of circuitry to provide heat to heater 40 and promote detachment. In one example, the detachment system provides a cue to the user when the link is aligned appropriate with the contact. The user could then take an action (i.e. press a button on the user interface) which would engage the parallel system to heat heater 40 and detach the coil segment.

In another embodiment no cue is provided to the user when the link is appropriately aligned. Instead, the user may take an action (i.e. press a button on the user interface) when detachment is desired. Then when the link is appropriately aligned the detachment sequence will commence. The heating of heater 40 could, as described earlier, be part of a parallel or integrated system.

The coil detachment systems shown in FIGS. 4-7, 8, 13-16 illustrate a type of intelligent microcatheter, where microcatheter 22 has means near the distal end of the microcatheter to read the embolic coil position via contacts. Other embodiments of the various systems described could utilize a hypotube, smaller microcatheter, or other delivery device delivered through a microcatheter. The coil would be delivered through this hypotube/smaller microcatheter/inner delivery device, where the hypotube/smaller microcatheter/inner delivery device would have the contacts to read the embolic coil position.

Figure 17:
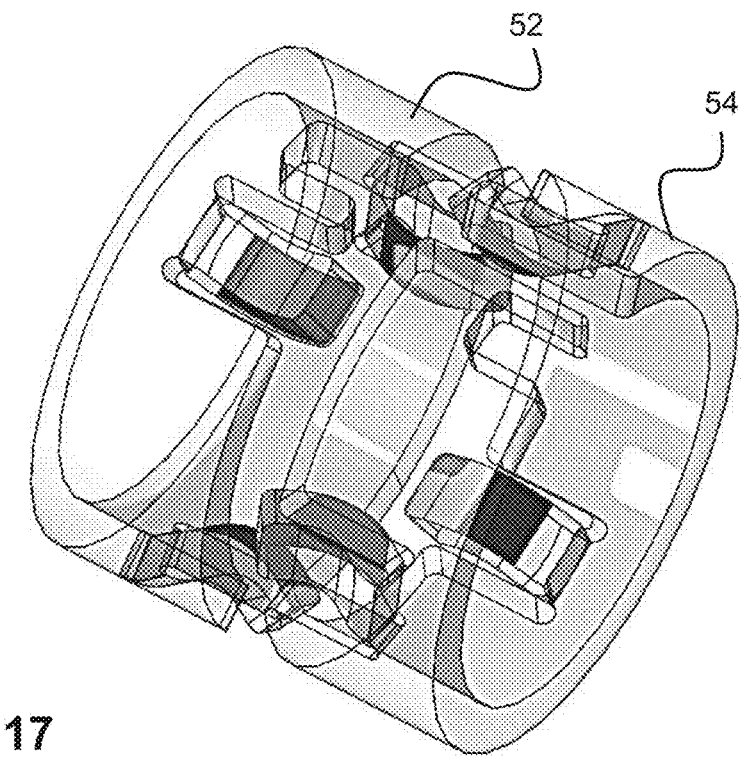
FIGS. 17-20 illustrate a contact that can be used in an embolic coil detachment system.
Figure 18:
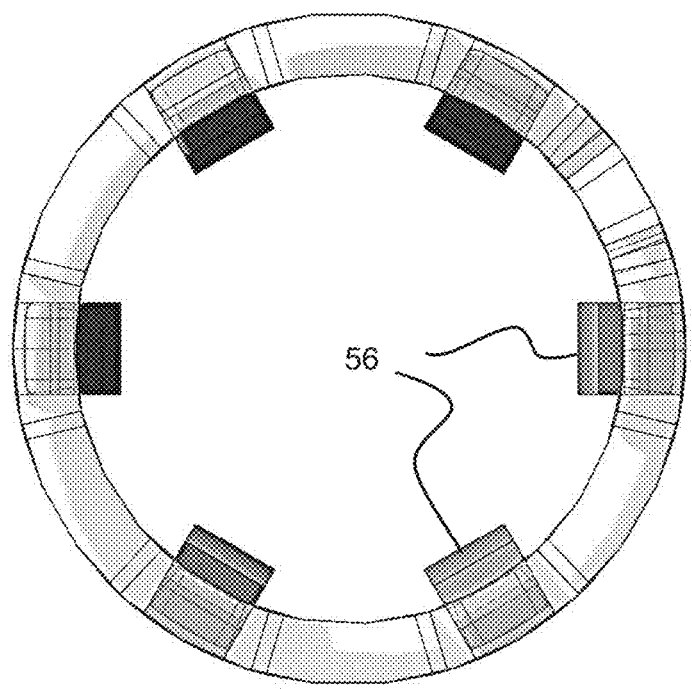

FIGS. 17 and 18 show one embodiment of contacts 52, 54 in which the contacts 52, 54 are ring or cylindrically shaped. The contacts 52, 54 can be made of nitinol, spring steel, stainless steel, or similar materials and have conductive tips 56 comprised of a conductive material such as gold and are best seen in the top, profile view of FIG. 18. As the embolic coil passes by, the tips 56 contact different areas, providing electrical communication with the rings 52, 54.

For the correct detachment alignment, the tips 56 line up with conductive sleeves 34, 35 to complete the circuit. Detachment can then be initiated by the user if desired. The contacts are connected to the control system which can include positive and negative voltage terminals on the voltage source to appropriately polarize the contacts. Thus contact 52 can be positive and contact 54 can be negative, or vice-versa.

Figure 19:
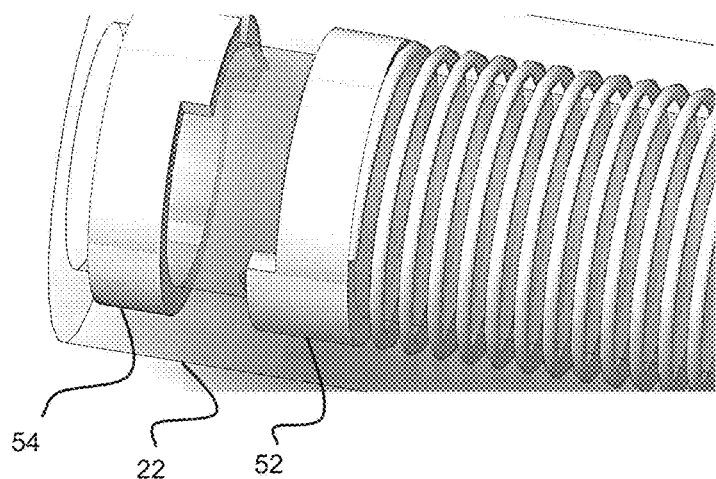

FIG. 19 shows contacts 52, 54 being located within a microcatheter 22. In this figure the contacts 52, 54 are embedded in the region between the inner and outer diameters of the microcatheter (i.e., within the microcatheter wall), near the distal end of said microcatheter. The necessary circuitry can also run lengthwise along this region, through the microcatheter. Alternatively, a conductive element besides wires (i.e. a conductive sleeve or conductive trace) could run lengthwise through a particular region of the microcatheter to connect back to the control system. In another example these contacts may be located on the outside of the microcatheter. In another example these contacts may be located at the periphery of the inner lumen region.

Figure 20:
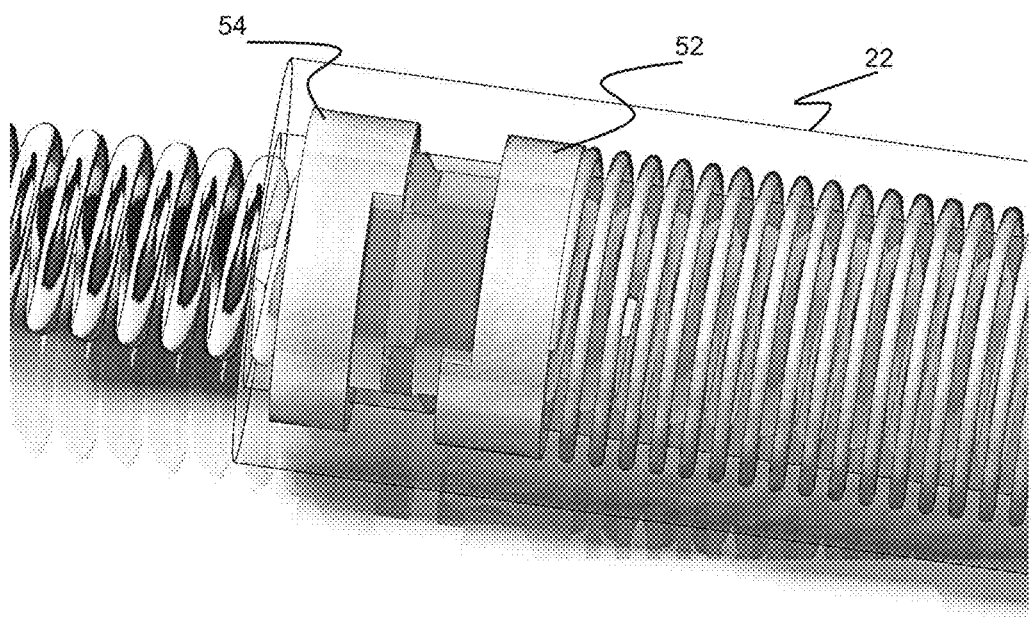

FIG. 20 shows the system as an embolic coil passes through. The contacts 52, 54 are embedded within the microcatheter and are connected to a voltage source at the other end (one contact to a positive and another contact to a negative terminal). Alternatively, other voltage sources such as an alternating-current system can be used. As described earlier, when the coil passes through, the circuit will be completed when the detachment zones are lined up correctly with the contacts 52, 54 and the tips 56. Thus when the conductive sleeves 34, 35 line up correctly with contacts 52, 54 the circuit will be complete and detachment can be initiated if desired in the manner described earlier.

In one embodiment, the coil segments 12 that make up the embolic coil (e.g., 10 or 11) may utilize various types of coil. For example, often when filling aneurysms a relatively firmer framing coil is deployed first to frame the periphery of the aneurysm. A relatively softer filling coil is then used to fill the space within the aneurysm. An even softer finishing coil is finally used to fill the small spaces left within the space of the aneurysm.

An embolic coil used in the embolic coil detachment system could utilize some segments of the embolic coil as framing coils, some segments as filling coils, and some segments as finishing coils. In one example, the distal most coil segment would be a framing coil, the next-distal most segment would be a filling coil, and the most proximal segment would be a finishing coil. In another example, the distal most coil segment would be would be a framing coil and the next segment would be a filling coil. In another example, the distal most coil segment would be a filling coil and the next segment would be a finishing coil. Alternatively, various combinations of framing, filling, and finishing coils could be used as coil segments of the embolic coil. Operation time could be sped up considerably by having one embolic coil with various coil segments comprising the different types of coils necessary for aneurysm/malformation treatment.

In another embodiment the coil segments comprising the embolic coil may utilize the same type of coil. In one example one of the embolic coils could be comprised of only framing coils, another only of filling, another only of finishing coils. The ability to detach the coil at various points would customize the coil length to the specific aneurysm/malformation volume, at which time the next type of coil could be introduced if necessary. In one example, a first embolic coil utilizes framing coil segments. This is introduced first, and then detached at the appropriate detachment zone when desired. A second embolic coil utilizing filling coil segments is then used and detached at the appropriate detachment zone when desired. Finally, a third embolic coil utilizing finishing coil segments is then used and detached at the appropriate detachment zone when desired.

Various methods of delivering and/or utilizing an embolic coil and/or an embolic coil detachment system are also contemplated. A method of delivering an embolic coil may utilize providing an embolic coil with detachment regions, delivering such a coil through a delivery device, and initiating a detachment sequence utilizing the detachment system to detach all or a portion of the coil in the vasculature. A method of utilizing the detachment system may involve providing a coil with variable detachment regions, then utilizing a detachment sequence when appropriate to detach all or a portion of the coil within the vasculature. Indication means may optionally be provided to alert the user when the detachment regions are properly aligned.

Other methods contemplated include providing an embolic coil having multiple coil segments wherein each segment comprises a unique type of coil (i.e. framing, filling, or finishing coils), delivering this coil through a delivery device, and selectively detaching each of the coil types utilizing the detachment system. Another method could include providing various embolic coils where each coil is comprised of a different type of coil (i.e. one coil having only framing coil segments, another coil having only filling coil segments, another coil having only finishing coil segments). The first coil is delivered through the delivery device, and a detachment sequence is initiated when desired. The next coil is then delivered through the delivery device, and a detachment is initiated when desired, and so-forth.

The methods discussed are not intending to be limiting and only highlight examples of how the devices, techniques, and embodiments described above could also utilize various methods of operation.

Figure 21:
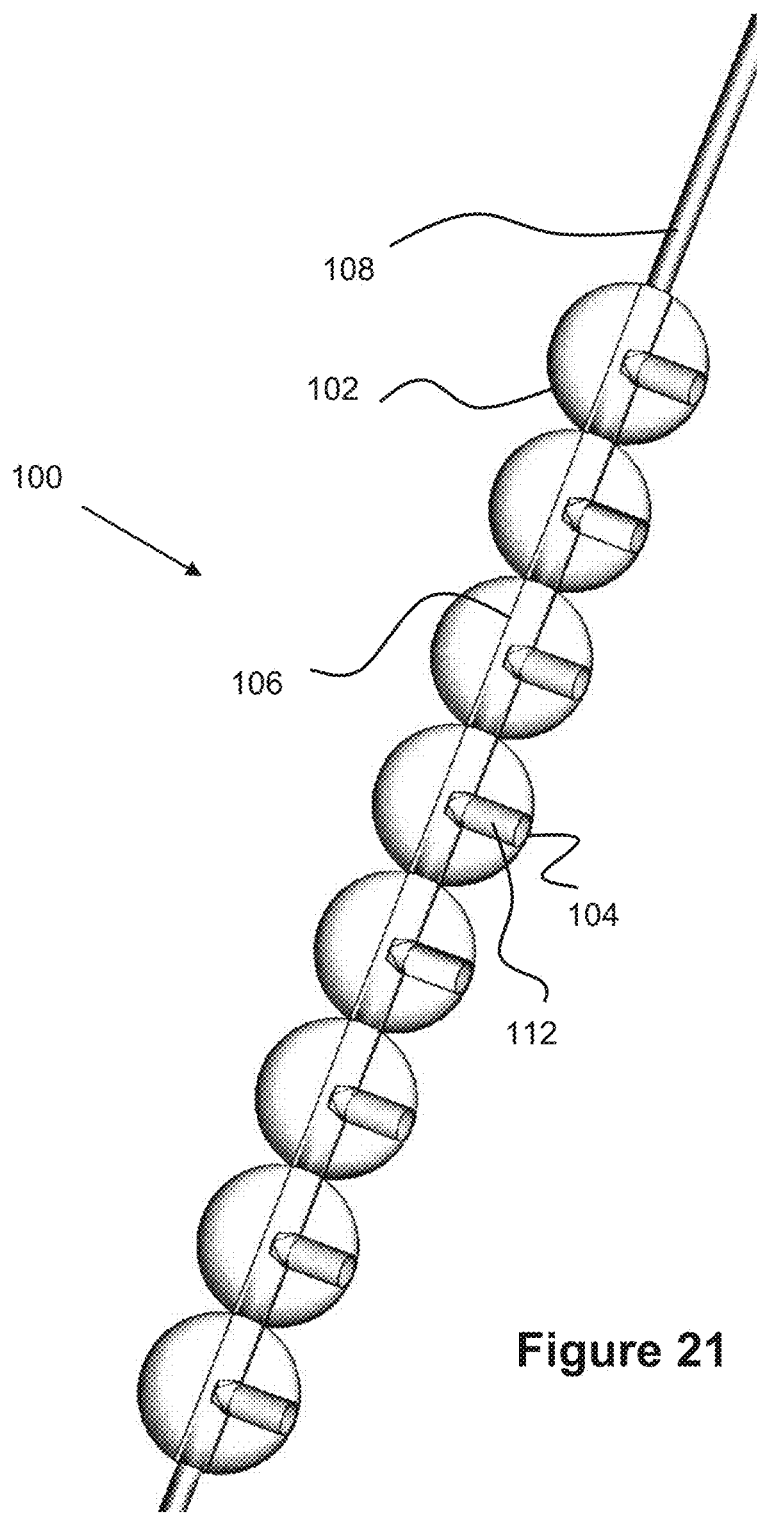
FIGS. 21-22 illustrate an embolic chain of spheres.
Figure 22:
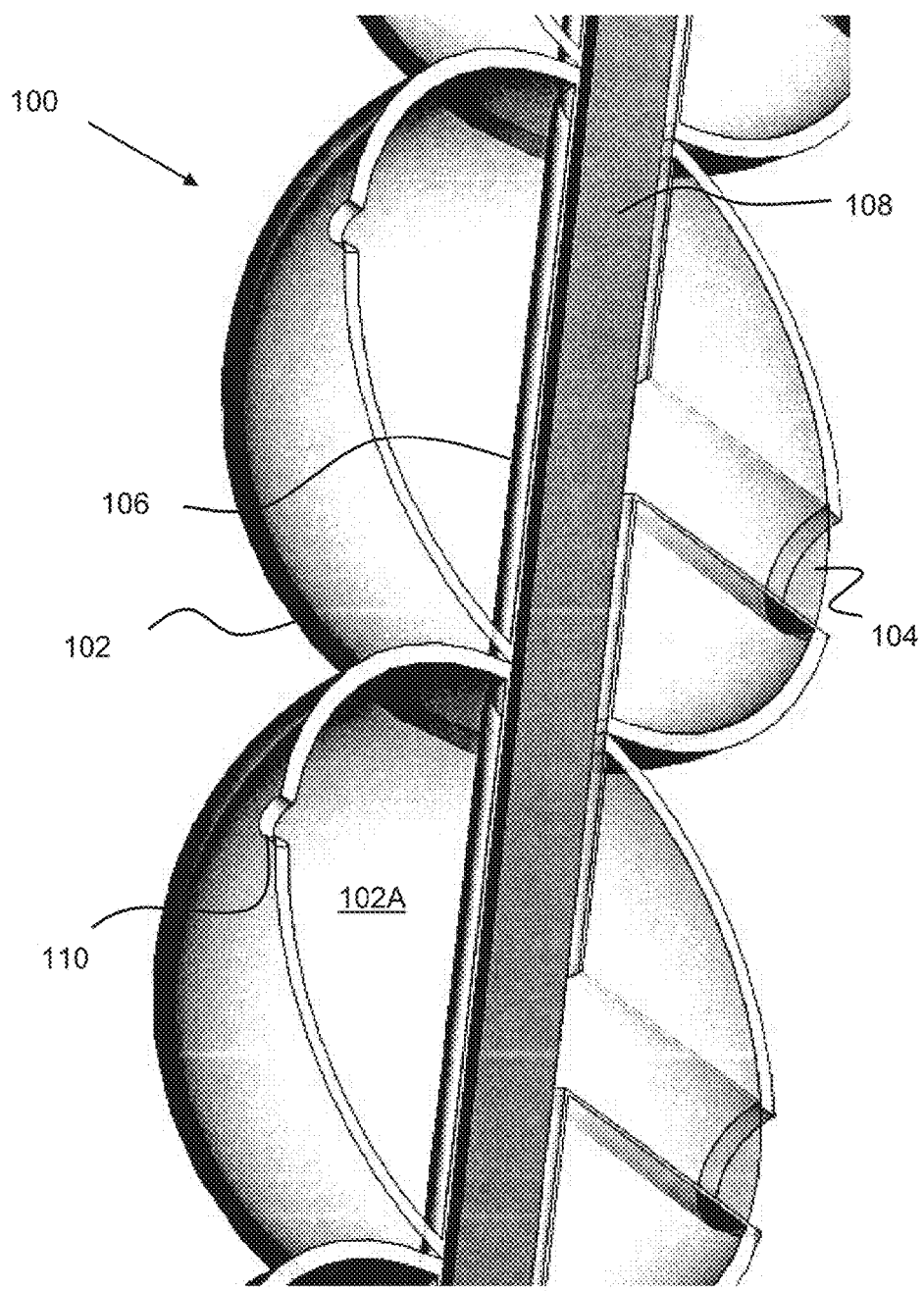

FIGS. 21 and 22 illustrate an embodiment of a detachable embolic sphere chain 100 that can be used similarly to the previously discussed embolic coils. Preferably, each sphere 102 includes a passage 106 that extends there through, allowing a monofilament or tether member 108 to pass through. In one embodiment, the spheres 102 can be anchored to the monofilament 108 by injecting adhesive 112 through passage 104, which opens to the monofilament passage 106 and thereby binds to both the sphere 102 and monofilament 108. Preferably, a plurality of spheres 102 are fixed on a monofilament 108, adjacent and in contact with each other.

As best seen in FIG. 22, the spheres 102 are hollow, forming an internal cavity or lumen 102A which can contain hydrogels, foams, and/or drugs that can be released in a patient via aperture 110. Various aspects of the aperture 110 can be adjusted so as to increase or decrease the speed that the materials are released at. For example, the diameter and depth of the aperture 110 can be adjusted to allow surface tension and capillary action to be the primary mechanism of dispersing material. In this respect, decreasing the aperture size or increasing the aperture depth (i.e., the thickness of the walls of the sphere 102 around the aperture 110) may decrease the rate of delivery of the material. In another example, the aperture 110 can be designed so that at normal atmospheric pressure the material (e.g., drug) is stable within the sphere 102 but when the sphere 102 enters the vasculature of the patient, a gradient is formed that drives the drug out of the sphere 102. In yet another example, a bio-absorbable or biodegradable plug (e.g., PGLA) can be placed into the aperture 110 and can have various thicknesses, depending on the length of time desired for drug delivery to begin (e.g., minutes, hours, days, or even months).

The spheres 102 may be composed of a metal, such as platinum, palladium, Nitinol, tantalum, or stainless steel. Alternately, the spheres 102 may be composed of a polymer that is plated with a conductive material. For example, where a 0.017' catheter lumen is used, spheres of 0.013"-0.016" diameter may be used. However, this is only offered as an illustrative example and various sizes are contemplated and can be used with various sizes of catheters.

Generally, the sphere chain 100 can be used with any catheter that includes electrical contacts within its lumen, such as any of the catheter embodiments discussed in this specification. In one embodiment, the monofilament 108 is made of a metal or conductively-plated polymer (e.g., polyimide plated with gold), which allows current to be conducted between two or more spheres 102 (e.g. when the electrical contacts are axially spaced inside the catheter lumen). Hence, current conducts through one sphere 102, into the monofilament 108, though an adjacent sphere 102, and out through a second contact, thereby heating up the monofilament 108, melting the polymer, and separating the two spheres 102.

In another embodiment, a non-plated polymer monofilament 108 can be used to connect the spheres 102. In this respect, current would pass from one sphere 102 directly to an adjacent sphere 102 via their contact with each other. This current would cause the two spheres 102 to heat up, melting and breaking the monofilament 108.

Though the term sphere is used to describe elements 102 of the chain 100, other shaped members could alternately be used. For example, cylinders, cubes, hollow saddle shapes, or similar multi-sided shapes. Thus, the term spheres is not meant to be limited to only spherically shaped elements 102.

In one embodiment, the monofilament 108 is tensioned between spheres 102 so as to maintain contact between each of the spheres 102. In another embodiment, the monofilament 108 is not under tension between the spheres 102.

While the monofilament passage 106 is shown as being straight, a curved passage is also possible. In this regard, the openings of the passage 106 would not be parallel to each other. It is further contemplated that several spheres 102 with curved passages 106 can be used to impart a secondary shape to the chain 100.

In another embodiment, the spheres 102 may further have a wire coil disposed over its outside surface. For example, a single coil may cover the entire chain 100, or a plurality of smaller coils may each cover one or more of the spheres 102.

Figure 23:
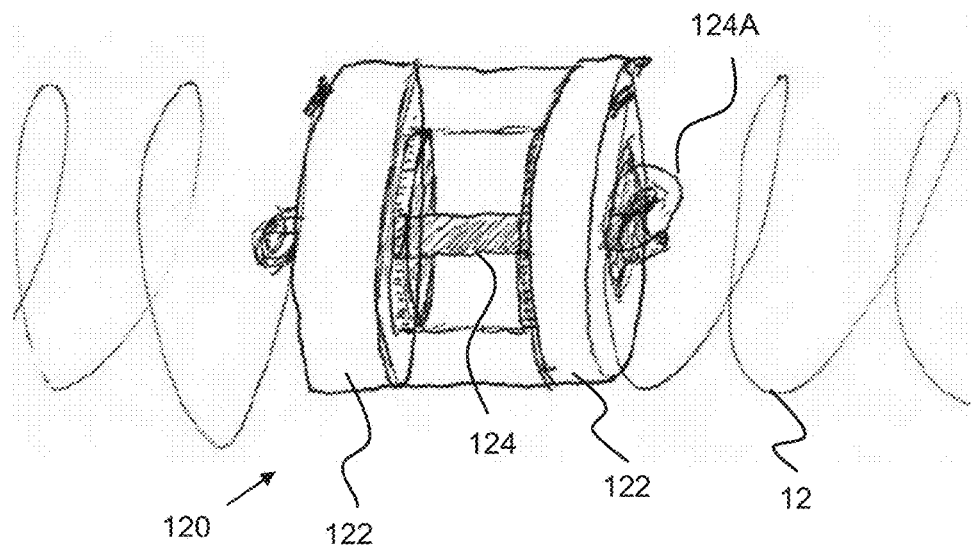
FIG. 23 illustrates a severable joint for an embolic coil.
Figure 24:
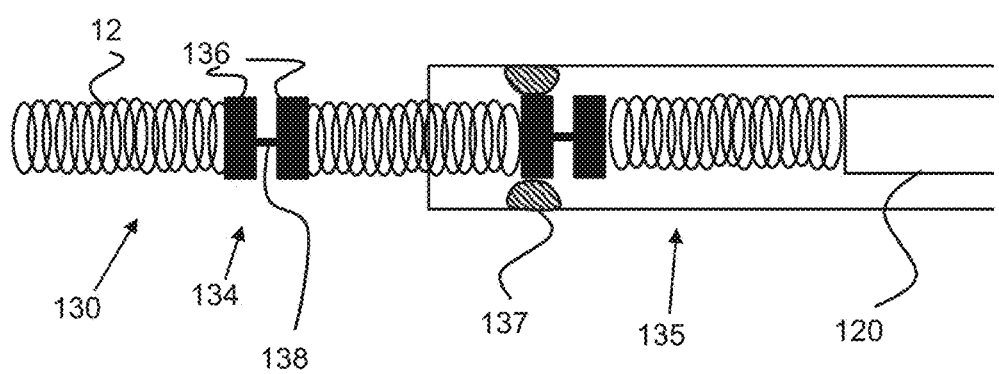
FIG. 24 illustrates an embolic coil with a plurality of joints that can be severed by electrical contact with a catheter's electrode.

FIG. 23 illustrates another embodiment of an embolic coil having a joint 120 that can be selectively released to separate two coil segments 12 from each other. The joint 120 includes a fuse link 124 that is connected to two contact bands 122. In one embodiment, the fuse link 122 extends through an aperture of the contact bands 122 and forms a knot 124 to maintain tension between the contacts. In one example, the fuse link 124 is composed of a polyimide monofilament or hypotube that is plated with gold or a similar conducting material. When the contact bands 122 become aligned with electrical contacts within a catheter (e.g., such as any of the previously described catheters within the present specification), electrical current flows through the fuse link 124, fracturing the plating and breaking the polyimide. Hence, the joint 120 separates, disconnecting one segment 12 from another. As with other embodiments described in this specification, a microcoil may have several of the joints attaching multiple coil segments 12, which allow the operator the option of detaching portions of the coil FIG. 24 illustrates yet another embodiment of a microcoil 130 having a plurality of electrolytically detachable joints 134. The joints 134 preferably include a conductive ring 136 connected to the end of each coil segment 12 and an electrolytic link 138 that couples two of the rings 136 together. The microcoil 130 is preferably connected to a power source at the proximal end of the pusher 120, while contact 137 is connected to a different polarity terminal of the same power source. When the microcoil 130 is aligned so that electrical contacts 137 contact a distal ring 136 of the joint 134, a circuit is created. Specifically, a circuit path begins at a proximal end of the pusher 120, passes through the coil segments 12, through a proximal ring 136, through the electrolytic link 138, through the distal ring 136, through contact 137, and back to the power source. When voltage is applied to this circuit, the electrolytic link begins to electrolytically degrade, thereby releasing the portion of the microcoil 130 that is distal of the joint 134.

In one embodiment, the microcoil 130 and pusher 120 can be plated in gold or other high conductivity plating material to enhance electrical conductivity. In another embodiment, instead of an electrolytic link 138, other types of links can be used, such as thermal, thermal-mechanical, RF, mechanical, and optical.

Figure 25:
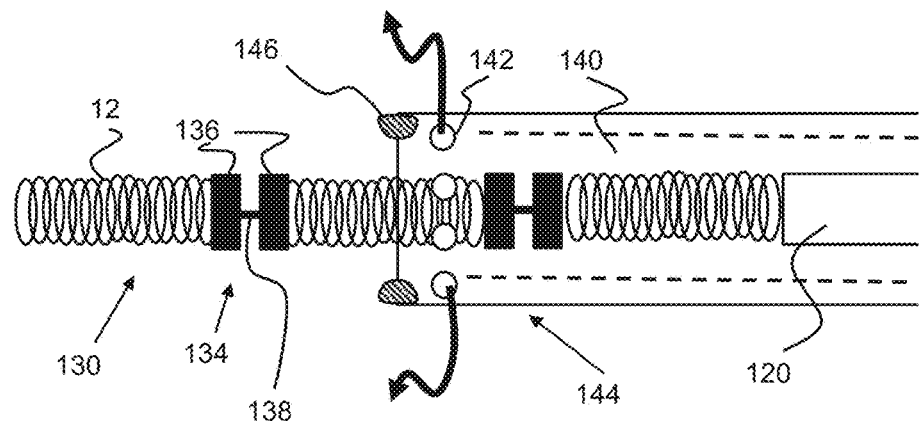
FIG. 25 illustrates a catheter that breaks an electrolytic joint on an embolic coil.

As seen in FIG. 25, the microcoil 130 can also be used with a somewhat different catheter 144 in which the catheter's electrical contact 146 is located at the distal end of the catheter 144, creating a circuit between the contact 146, through the blood of the patient, and into the microcatheter 130. To prevent all of the links 138 still within the catheter 144 from electrolytically degrading, a purge fluid 140 that does not conduct electricity (e.g., a fluid with about 0 parts-per-million of salts or ions) is pumped into the catheter's lumen. To prevent this non-conducting fluid from interfering with degrading the joint 134 that is immediately distal of the catheter's end, purge holes 142 (or alternately slits or similar shapes) connecting to the catheter's lumen are positioned proximal to contact 146. In this respect, the non-conducting purge fluid 140 exits the catheter 144 proximally of the contact 146, allowing conductivity between the joint 134 and the contact 146. In one example, the non-conducting fluid 140 can be iodine, which also allows a user to view the fluid under X-rays and can be more viscous so as to better remain in the catheter. Generally, this embodiment decreases or eliminates the need for precise alignment of and contact between the joint 134 and the contacts within the catheter, since the patient's blood carries a majority of the current. In one example, the electrolytic link 138 is composed of stainless steel and the coil segments are composed of platinum.

Figure 26:
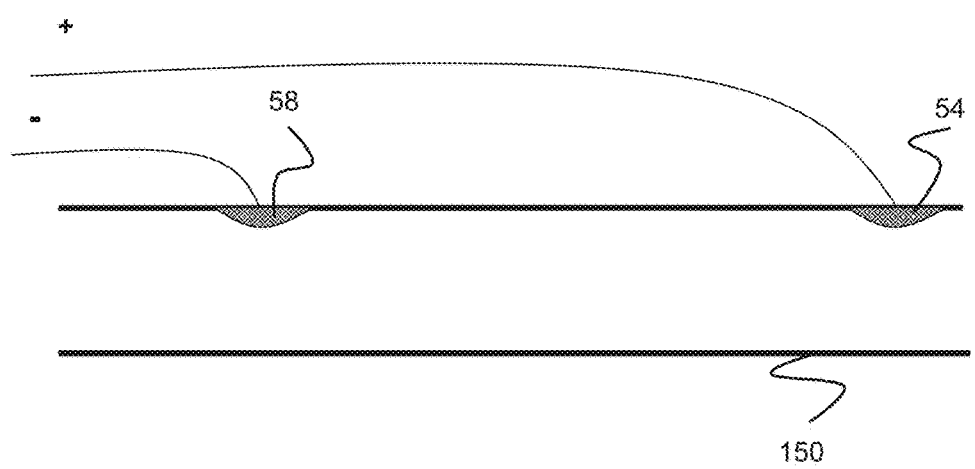
FIG. 26 illustrates a catheter used in a guidewire steering system

FIG. 26 illustrates an embodiment of a catheter 150 used for a guidewire delivery system. The catheter includes a proximal electrical contact 58 and a distal electrical contact 54, which are oppositely polarized from a proximal power and control system. There may be a user interface (i.e. a button) which the user can use to interface with the control system (e.g., similar to control/power systems described with regard to other embodiment of this specification). Though contact 54 is shown as having a positive polarity and contact 58 is shown as negative, these can be reversed. The contacts can be similar in design to contacts of FIGS. 17-18.

Figure 27:
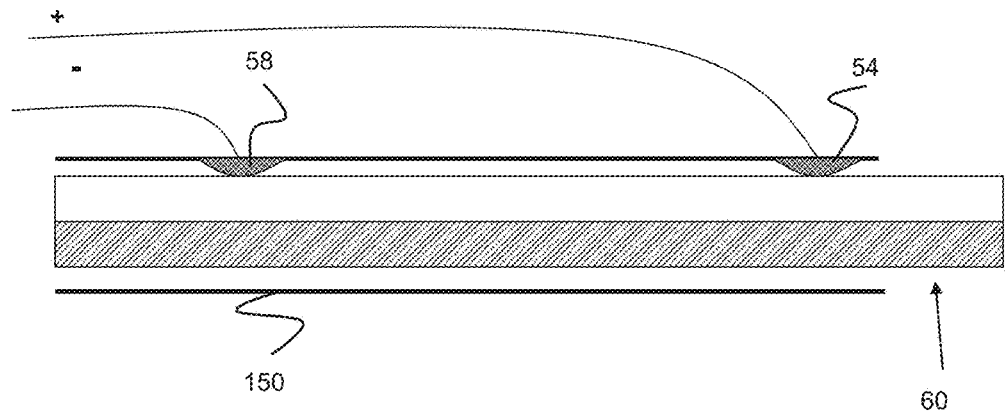
FIGS. 27-28 illustrate the catheter from FIG. 26 with a guidewire being delivered through the catheter
Figure 28:
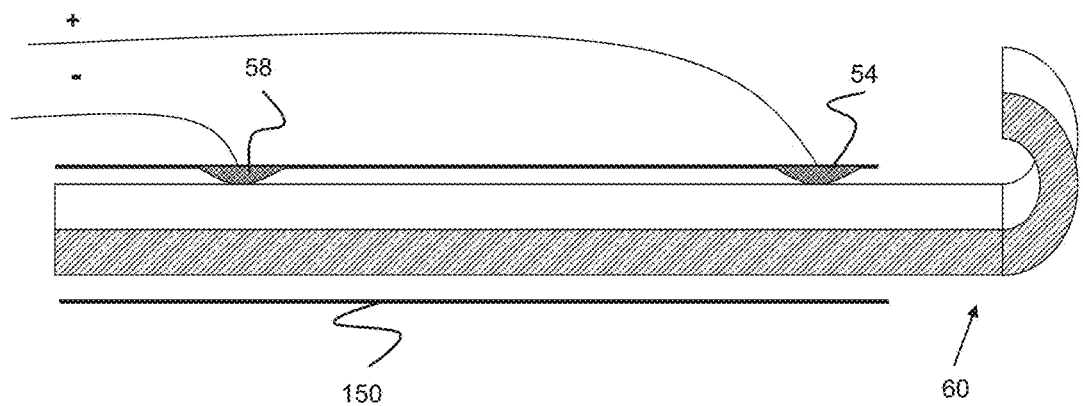

FIGS. 27-28 show the catheter used with a guidewire 60. The guidewire 60 is preferably made of a bimetal composite such that the guidewire 60 may bend when exposed to a sufficiently high temperature. In one example, half of the guidewire 60 (i.e., half circle of the guidewire's cross section) is composed of a first metal, while the other half is composed of a second metal with a different coefficient of expansion. When current is applied to the guidewire 60 via contacts 54 and 58, the guidewire 60 increases in temperature. Since the metals expand at different rates, the guidewire bends in one direction. This bending can be used to help steer the guidewire 60 and catheter through the vasculature by bending the guidewire 60, rotating the guidewire 60 towards a desired direction, and further advancing the guidewire. In one example, only a distal portion of the guidewire 60 is composed of two metals on each side. In another example, the entire guidewire 60 comprises two halves that each are different metals.

Figure 33:
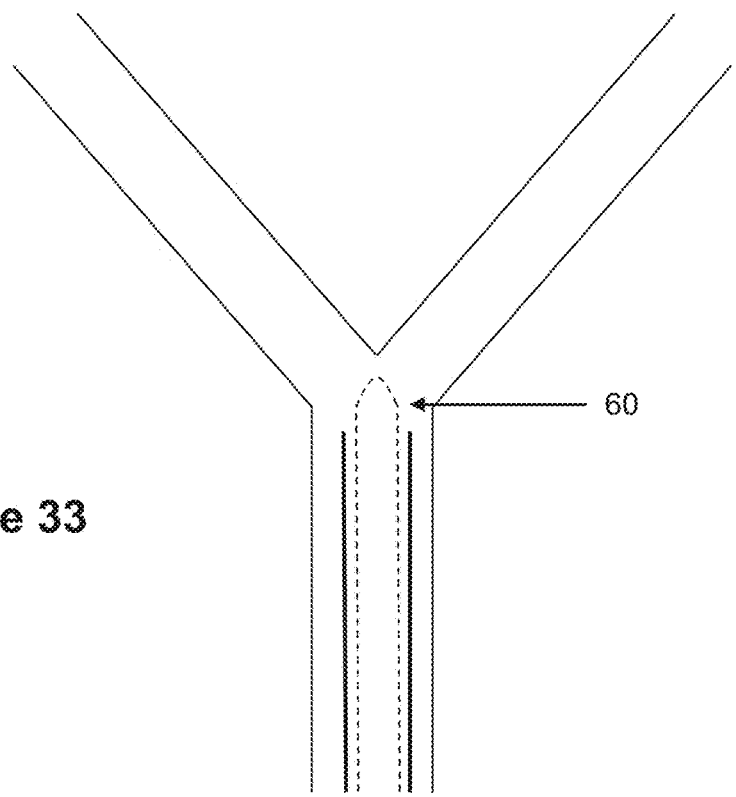
FIGS. 33-34 illustrate a bendable guidewire within the vasculature.
Figure 34:
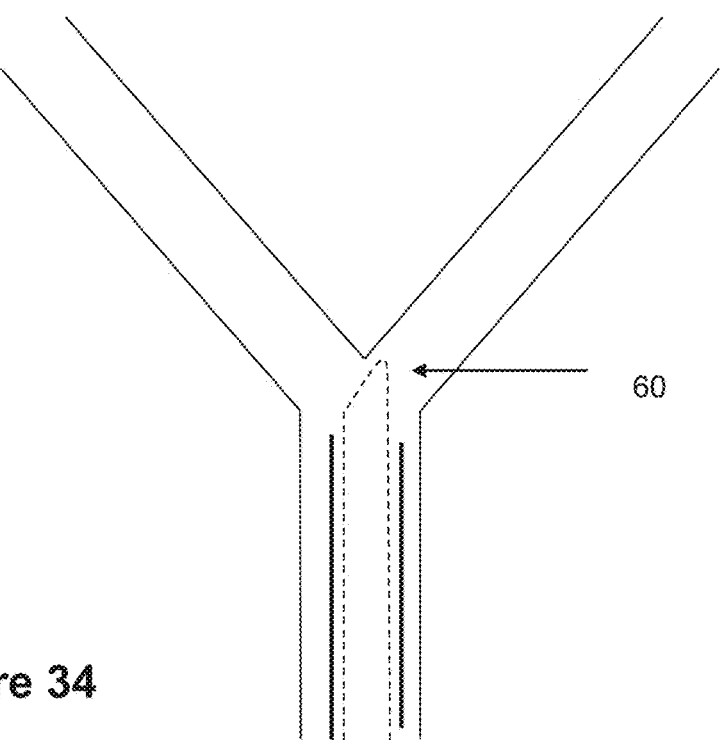

In one method of use example, the catheter 150 may reach a bifurcation in a vessel and the steering system can be enabled (via the user interface) to cause the distal end of the guidewire 60 to bend. The user can then torque or rotate the catheter 150 and guidewire 60 so the bend is directed in the direction he or she desires to steer the catheter (see FIGS. 33-34). In order to create a sufficiently high temperature increase to cause the guidewire to bend, the contacts are preferably spaced out to allow a higher current flow path to increase heat transmission. In one example, this spacing is from about 0.5 to 3 cm. Factors such as the materials used and electrical impulse utilized can affect the required spacing between the contacts.

Figure 29:
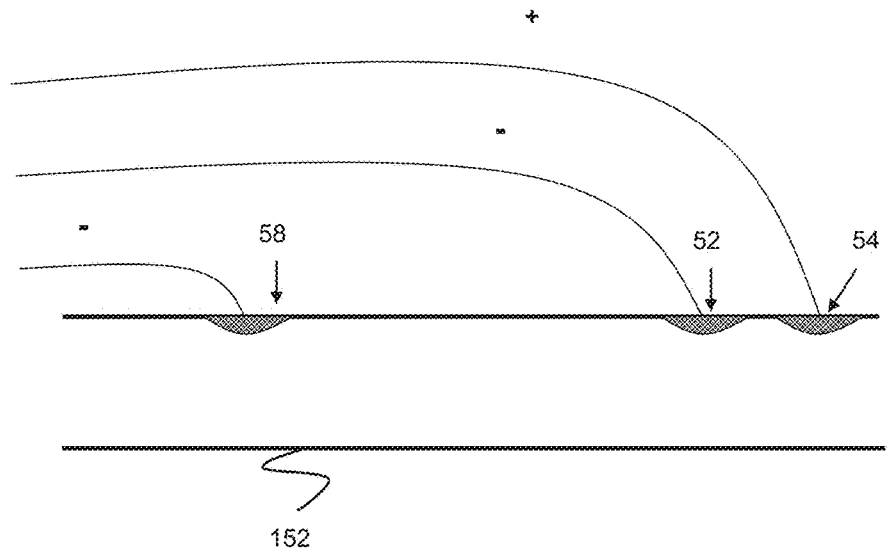
FIG. 29 illustrates a catheter used in a combined embolic coil detachment and guidewire steering system

FIG. 29 shows a catheter 152 used in a combined guidewire-embolic coil system. The catheter utilizes three contacts 52, 54, 58. The more distal contacts 52, 54 are used with the embolic coil detachment system (e.g., any of the embolic coils discussed in the present specification) while contacts 54, 58 are used with the guidewire 60. Contacts 52, 58 preferably have the same polarity while the distal-most contact 54 has an opposing polarity. Though contact 54 is shown as being positively polarized and 52, 58 are shown as being negatively polarized, it could be switched such that 54 has a negative polarity and 52, 58 have a positive polarity. In one example, a user interface could have two buttons to interact with the guidewire system or the embolic coil detachment system. The contacts 52, 54, 58 are similar to the contacts shown in FIGS. 17-18.

In another embodiment a catheter/delivery device (i.e. sheath, hypotube, microcatheter, or catheter) utilizes electrical contacts. The catheter can be thought of as an intelligent catheter since it comprises electrical contacts which interact with devices placed through said catheter. The contacts are connected to an electric system to polarize the contacts. The contacts can be used to interact with devices which pass through the catheter (i.e. the embolic coil(s) and/or guidewire previously described). The user may have an interface to initiate a sequence (i.e. embolic coil detachment or guidewire manipulation) via the user interface previous described. In one example, for a combined embolic coil detachment and steerable guidewire system the user interface would have two buttons, one to detach the coil and another to bend the guidewire to aid in steering the delivery system. Hitting one button would send an impulse through the circuitry of the embolic coil detachment system, hitting the other button would send an impulse through the circuitry of the guidewire system. The intelligent microcatheter could utilize any of the contact structures shown and described in FIGS. 4, 8, 13, 21, 24.

Figure 30:
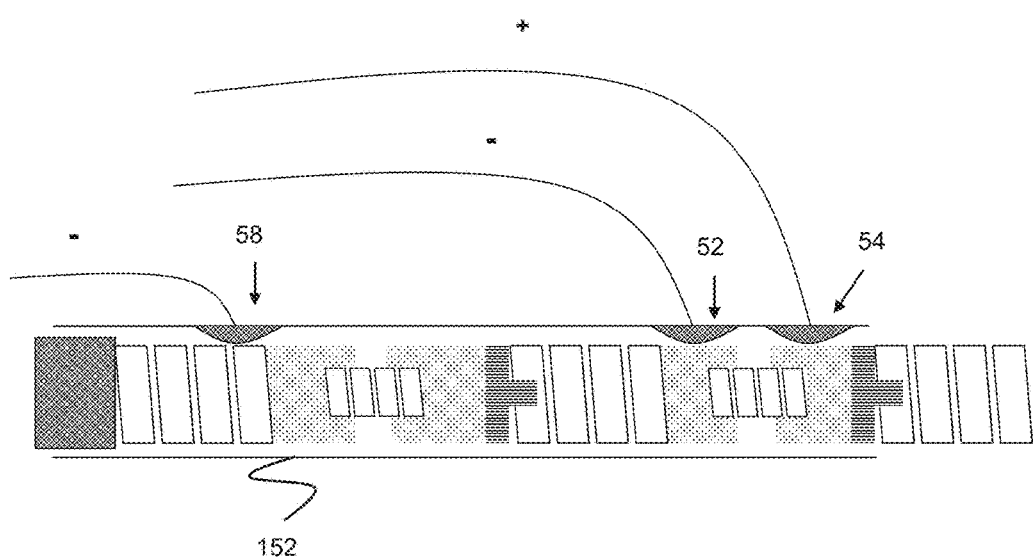
FIG. 30 illustrates the catheter from FIG. 29 used with an embolic coil

FIG. 30 shows the combined system used with an embolic coil. Contacts 52, 54 are used to interact with the coil and cause the coil segments to detach when the user desires so.

Figure 31:
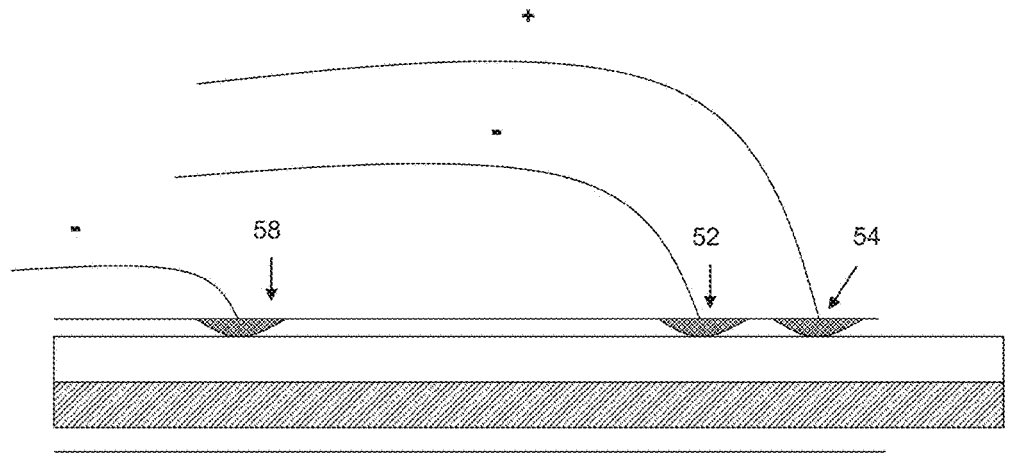
FIGS. 31-32 illustrate the catheter from FIG. 29 used with a guidewire
Figure 32:
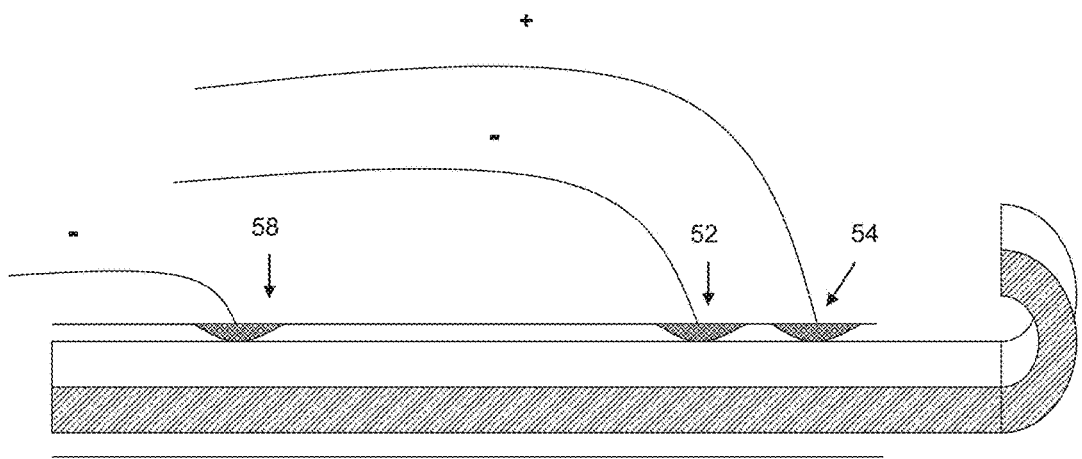

FIG. 31 shows the combined system used with a guidewire. Contacts 54, 58 are used to interact with the guidewire. In one example, the guidewire is almost as thick as the inner diameter of the delivery device/microcatheter to hit contact tips 56. In another example, the guidewire has enlarged diameter regions at selective areas in order to interface with the contact tips.

In another embodiment, contacts 52, 54 can be used in a combined guidewire-embolic coil system without the inclusion of the other proximal contact 58. In this embodiment, the guidewire would not need such a lengthy current flow path within the distal portion of the guidewire to cause the guidewire to bend, such that the additional proximal contact 56 is not necessary. The materials used in the bimetal composite and impulse used to generate the current are properties that could minimize the current flow path needed through the guidewire to cause the distal end of the guidewire to bend, which would be useful in this particular embodiment.

In another embodiment in lieu of a contact system, the guidewire itself could have a heater coil placed over the distal end of said guidewire. One end of the coil would have a positive polarity, the other end would have a negative polarity. A user interface would be coupled to the proximal end of the system, and a user could interact with the system to generate an impulse to send current through the heater coil to heat the distal tip of the guidewire to cause it to deflect. The user could then torque proximal end of the system to align the guidewire in a desired direction to aid in navigating the catheter through the vasculature. Alternatively, the guidewire has a heater coil placed over the distal end of the guidewire and the heater coil may electrically interact with a contact system built into the catheter (as described earlier) in order to heat the coil to cause deflection of the distal end of the guidewire. The heater coil would contact the electrical contacts of the catheter, the contacts are coupled to a user interface so the user could send an impulse through the system when desired. When the impulse is sent, the guidewire deflects in response to the heat generated via the heater coil, and the bent guidewire is then used to navigate the catheter.

In another embodiment in lieu of the heater coil placed over the distal tip of the guidewire, the microcatheter could have an integrated heater coil within the distal portion of the microcatheter. One end of the integrated heater coil would have a positive polarity, the other end would have a negative polarity. The coil could be integrated into a user interface coupled to the proximal end of the system, and a user could interact with the system to generate an impulse to send current through the heater coil. The heater coil could sit in close proximity to, or have direct contact with, the guidewire. When the guidewire sits at the distal end of the catheter, the user could heat the heater coil which causes the distal tip of the guidewire to deflect. The user could then torque proximal end of the system to align the guidewire in a desired direction to aid in navigating the catheter through the vasculature.

Figure 35:
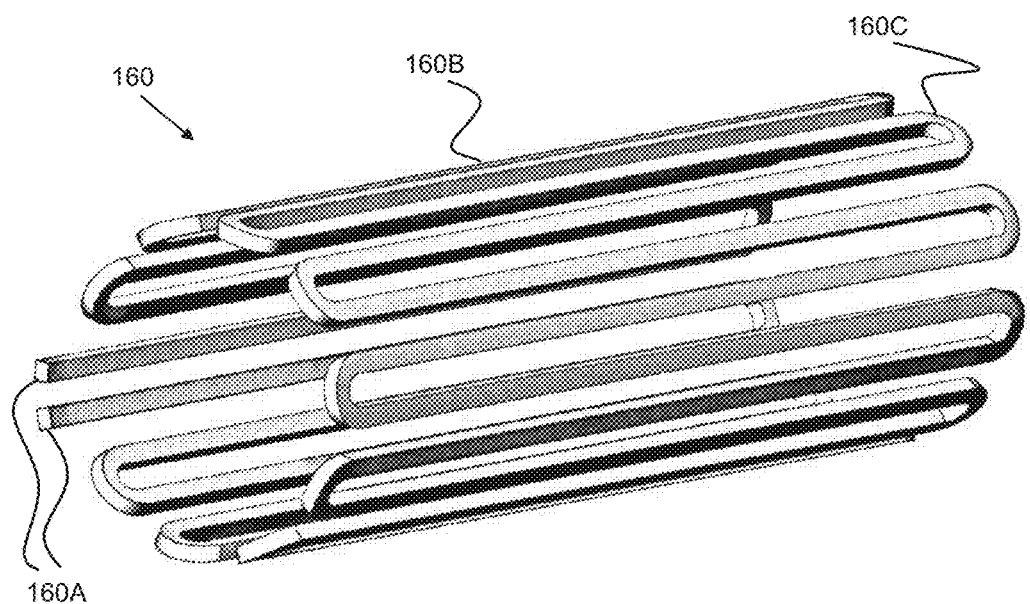
FIG. 35 illustrates a heater coil for a catheter system.

FIG. 35 illustrates an embodiment of a heater coil 160 comprised of a plurality of adjacent straight segments 160B that are connected to each other by a plurality of 180 degree curves. The pattern terminates with ends 160A that are connected to wires or similar conducting members that ultimately connect to a power supply and control system.

In one embodiment, a hypotube composed of a high resistivity metal, such as platinum, can be laser cut to this "zig-zag" pattern. In another embodiment, a thin sheet of metal can be laser cut in this pattern, then curved into a cylindrical shape. Preferably, the heater 160 is coated with an insulating material such as polyimide, polyethylene, Teflon, of paralyne. By creating the heating coil 160 by these techniques, the coil can have a relatively small thickness (e.g., such as 0.009") while still generating a significant amount of electrical resistance.

Figure 36:
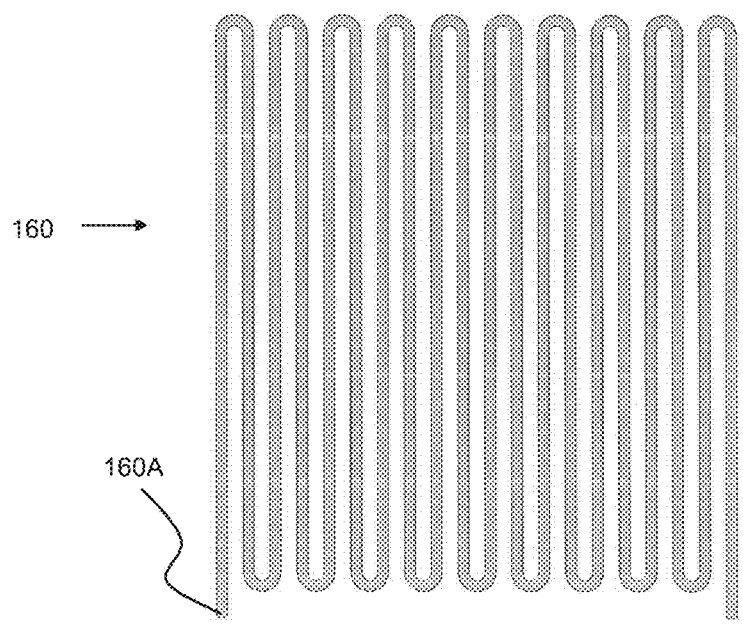
FIG. 36 illustrates a flat, laser cut sheet of material that can be used to form the heater coil of FIG. 35.
Figure 37:
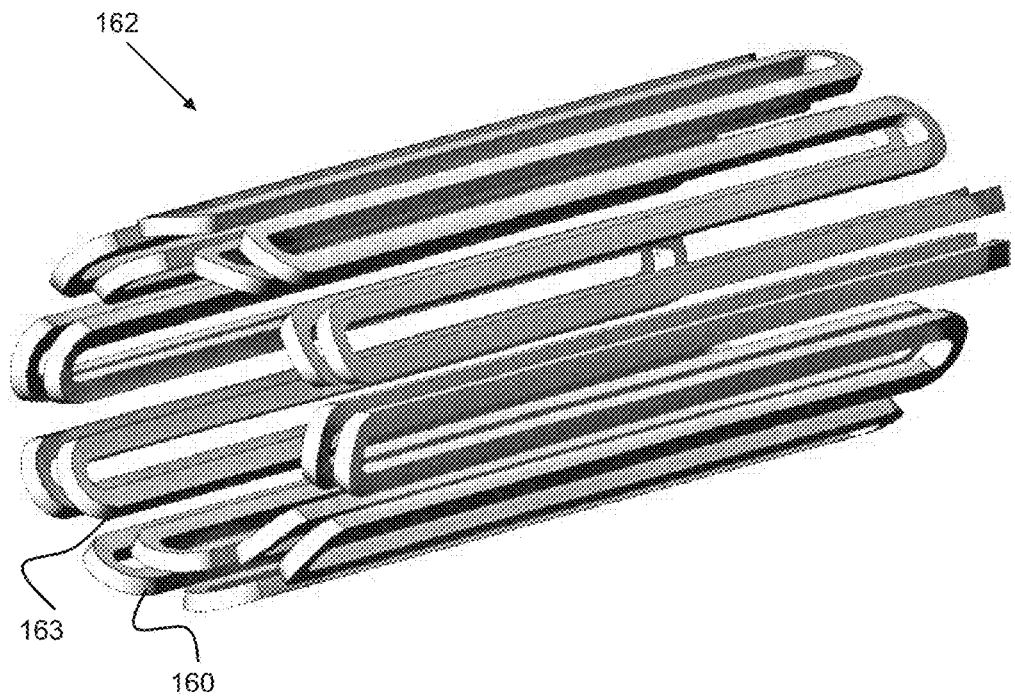
FIGS. 37-39 illustrate various configurations of multiple heaters from FIG. 35 within a catheter.

Since the heater coil 160 is relatively thin, one embodiment of a catheter could include a dual layer heater assembly 162 including the coil 160 and a second, small, inner coil 163 located within it, as seen in FIG. 37. Such an assembly 162 would allow the heater assembly 162 to provide a greater amount of heat to a catheter and/or provide redundancy. Other embodiments may include 3, 4, 5, 6, or more layers of heater coils. The layers of heater coils can each have independent electrical wires to supply power or each of the coils can be chained together in series. Alternatively, a single hypotube (FIG. 36) can be rolled into a multiple layer configuration where each successive roll of the hypotube becomes a new layer of the heater. With this configuration, only one set of wires would be needed to heat the whole system since the heater coil is comprised of the same hypotube pattern.

Figure 38:
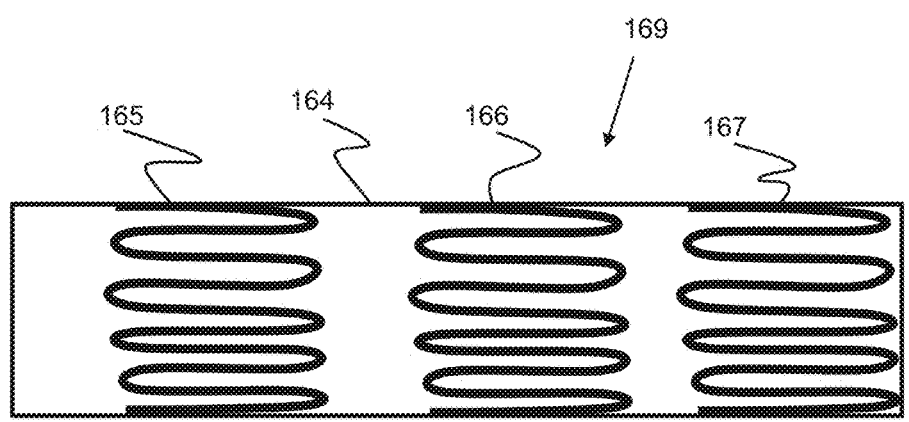

FIG. 38 illustrates another embodiment of a catheter heater assembly 169 that has a plurality of heater coils staggered along its length to create a plurality of independently operable heater zones. Specifically, the catheter 164 includes a proximal heater coil 165, a middle heater coil 166, and a distal heater coil 167, all of which are similar in design to coil 160. While three coils are shown, such a catheter could include any number coils (e.g., between 1 and 100 coils). The addition of different, discreet heater coils provides redundancy, temperature control, and/or user targeting of a detachment joint of an embolic coil.

Figure 39:
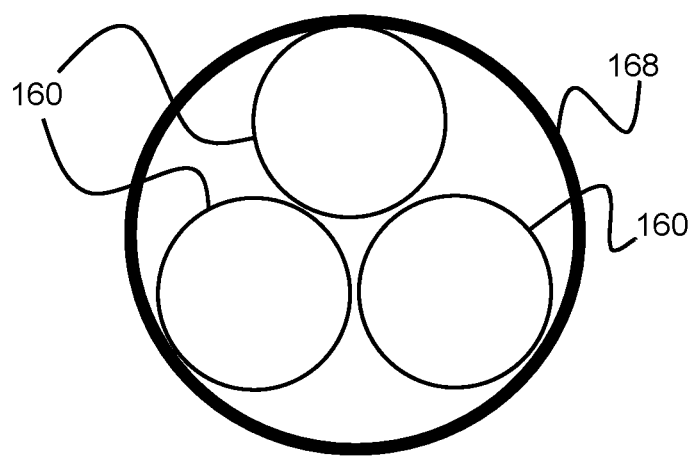

FIG. 39 illustrates a cross sectional view of yet another embodiment in which a catheter 168 has a plurality of heater coils 160 (e.g., 3 coils) that are positioned parallel to each other. Preferably, the coils 160 are each located within its own catheter lumen passage, thereby allowing several different devices to be used from the same catheter and heated (e.g., for detaching an implant or bending a guidewire as previously described).

As discussed in greater detail below, FIGS. 40-70 disclose various additional link or joint embodiments that connect various segments of an embolic device together and that can be selectively separated by a user. While coil portions 12 are described with regard to these embodiments, it should be understood that any embolic device described in this specification could be used in connection with these joints, such as spheres 102.

Figure 40:
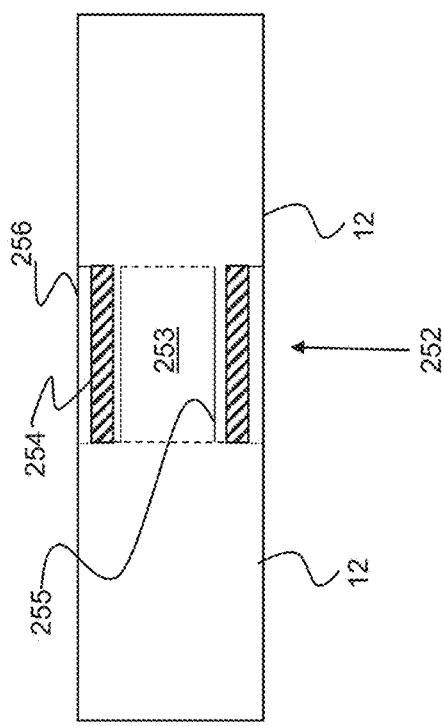
FIG. 40 illustrates another embodiment of an embolic device having a detachable joint.
Figure 41:
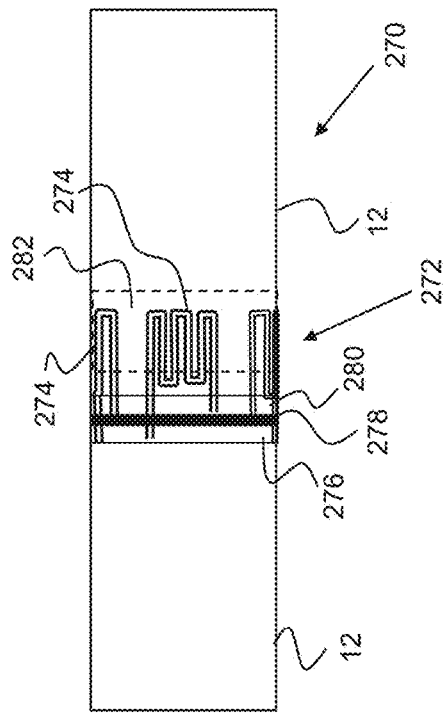
FIG. 41 illustrates another embodiment of an embolic device having a detachable joint.

Turning to FIG. 40, another embodiment of a detachment joint 252 that connects two portions of an embolic device, such as between coil portions 12. The detachment joint 52 is held together with a bond material 254 that can degrade (chemically or otherwise) when exposed to liquid such as blood, contrast, saline, or other commonly injected interventional fluids. For example, the bond material 254 may include a salt such as NaCl or similar salts that can dissociate into solution when exposed to liquid.

In one example, the bond material 254 can be selectively exposed to liquid via an outer electrically controlled membrane 256. When current is applied via any of the catheter embodiments described in this specification, the membrane allows fluid to enter the joint 252, allowing the bond material 254 (e.g., NaCl) to go into solution and the coil portions 12 to separate from each other. In one example, the outer membrane 256 operates via the Cassie-Wenzel wetting transitions effect, which is described in Bormashenko, Edward, Roman Pogreb, Sagi Balter, and Doron Aurbach. "Electrically Controlled Membranes Exploiting Cassie-Wenzel Wetting Transitions." Scientific Reports 3 (2013), the contents of which are hereby incorporated herein by reference.

In another example, outer membrane portion 256 can be a layer of hydrogel that, when an electric current is passed through via the catheter, causes the hydrogel to give off fluid itself and shrink. Once sufficiently shrunken, the hydrogel will allow fluid from outside the embolic device (e.g., saline from inside the catheter) to enter the joint 252 and degrade the bond material 254. In one embodiment, the hydrogel alone is used. In another embodiment, the hydrogel has a permeable film or layer over it.

In another example, the outer membrane 256 may be a thin film that melts or degrades when current from the catheter is applied to it. For example, this film could be composed of a polymer such as polyurethane or polyolefin with a melting point sufficient to melt via activation of the heater.

In alternate embodiments, the inner surface 255 of the joint 252 could be configured to selectively allow passage of fluid (e.g., saline or contrast) from the inner passage 253 to the bond material 254. This selective passage of fluid can be accomplished via any of the mechanisms discussed with regard to outer member 256, and can be used alone or in addition to the outer membrane 256 (i.e., both membranes can selectively allow passage of fluid).

FIGS. 41-45 illustrate various aspects of an embolic device 270 having coil portions 12 that are detachable from each other via joint 272. Generally, the joint 272 includes a plurality of heating elements 274 attached to a distal end of a coil portion 12 that, when activated, melt adhesive members 284, thereby releasing the adjacent coil portion 12.

Figure 42:
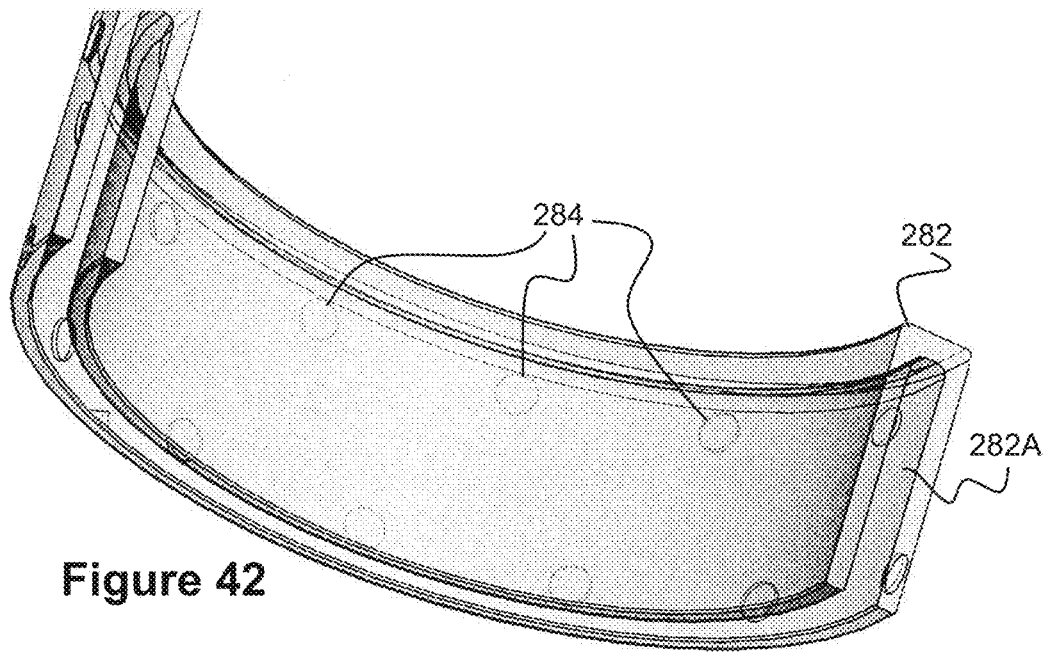
Figure 43:
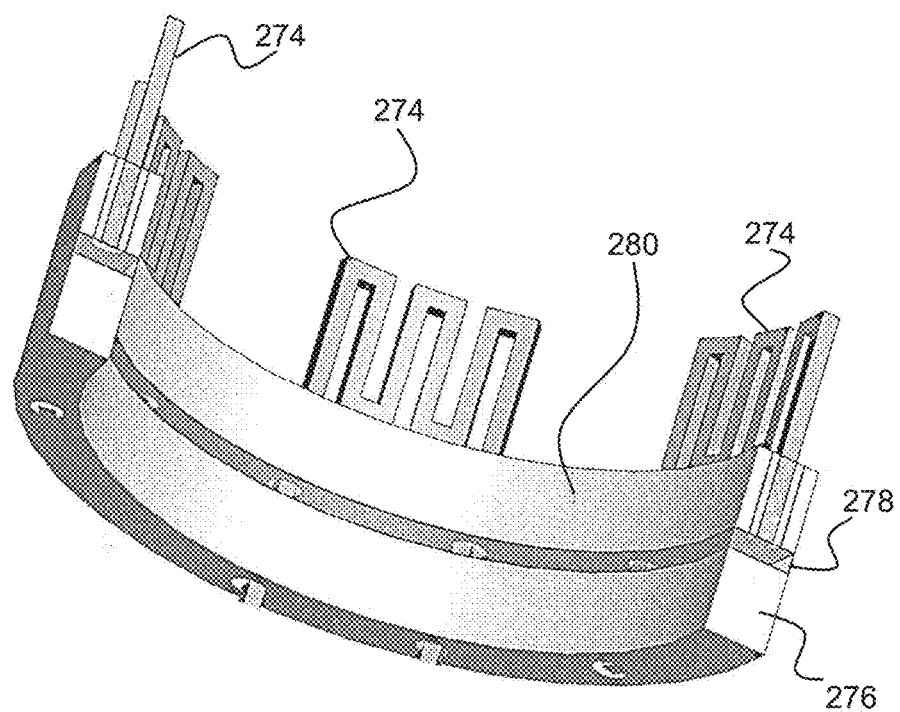

As best seen in FIG. 42, the adhesive members 284 are located within a groove 282A of a distal ring 282, which is fixed to a proximal end of another coil portion 12. The heating elements 274 are also positioned in the groove 282A, such that the adhesive members 284 fix or secure the heating elements 274 to the distal ring 282, thereby maintaining the two adjacent coil portions 12 together.

In one embodiment, the heating elements 274 form a plurality of generally rectangular shapes, though a variety of different shapes are possible, such as a single square or a plurality of circular loops.

Electrical current is distributed to each of the heating elements 74 via a distal conductive ring 280 and a proximal conductive ring 276 (both of which are separated by insulating layer 278). Each of the rings 280 and 276 can be contacted by current supplying elements within the catheter (described elsewhere in this specification).

The heating elements 274 preferably have a first end 274A that makes electrical contact with only the distal ring 280 and second end 274B that makes electrical contact with only the proximal ring 276. As seen in FIGS. 44 and 45, this arrangement can be accomplished by the first end 274A having a relatively small length that permits entry into only one of the apertures 280A of the distal ring 280, and the second end 274B having a relatively long length that extends through aperture 280, through the apertures of the insulating layer 278, and into one of the apertures 276A of the proximal ring 276. Insulating members 281 can be further located on portions of the second end 274B located within the aperture 280A of the distal ring 280, thereby preventing electrical contact that would otherwise prevent current from flowing completely through the heating element 274.

Figure 46:
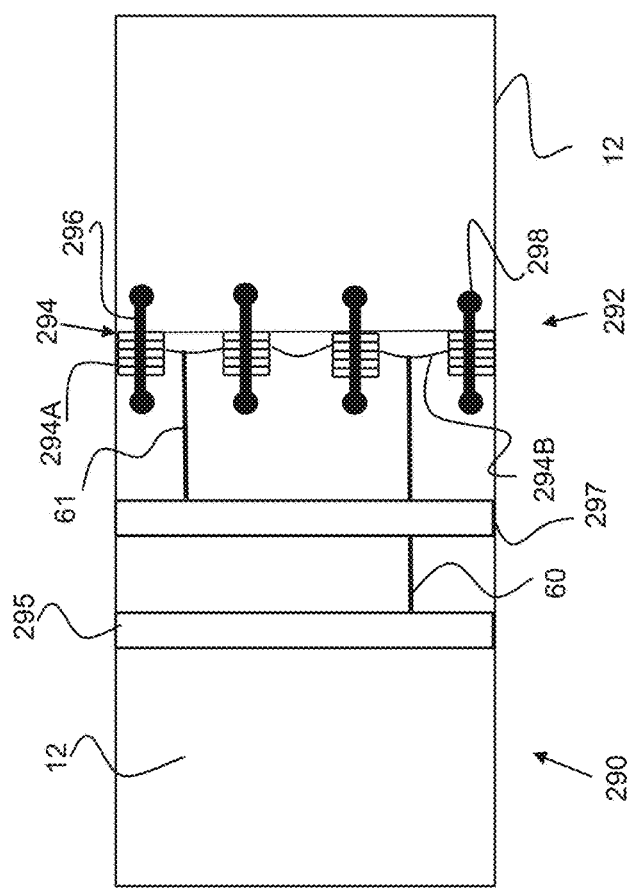
FIG. 46 illustrates another embodiment of an embolic device having a detachable joint.

FIG. 46 illustrates another embodiment of a segmented embolic device 290 with a plurality of joints 292 between adjacent coil segments 12. The joint 292 is held together by a plurality of tethers or monofilaments 296 located axially and circumferentially around the wall of the device 290. Each tether 296 is anchored under tension to both coil portions 12 via anchors 98. The anchors can be an adhesive, bonding agent, a distinct element that the tether 296 can be tied to, or similar fastening mechanisms.

Figure 47:
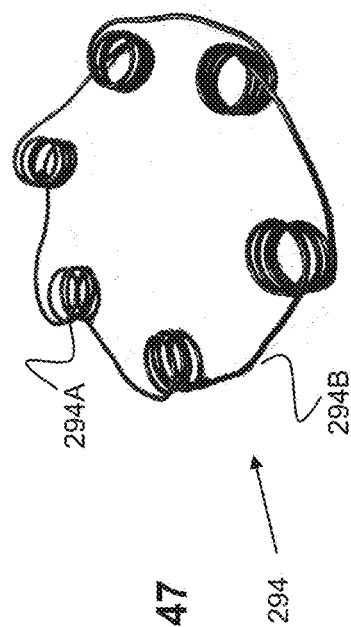
FIG. 47 illustrates a heater coil of the detachment system of FIG. 46.

The tethers 296 are preferably broken by a resistive heater 294 located near each of the tethers 296. For example, FIGS. 46 and 47 illustrate a resistive heater ring 294 that is composed of a plurality of coiled portions 294A connected by adjacent curved regions 294B, so as to form a ring shape. Each of the coiled portions 294A are preferably coiled around one of the tether members 296, so as to allow efficient heat transfer to the tether members 296. Finally, electric wires 60 and 61 are connected to portions of the heater 294 and each to an electrical contact ring 295 and 297. When the rings 295 and 297 align with electrical contact in a catheter (such as those described elsewhere in this specification) and current is applied by the user, the coils 294A heat up and melt or break the tether members 296 and release the coil portions 12 of the device 290 from each other, thereby releasing a portion of the device into the patient.

Figure 48:
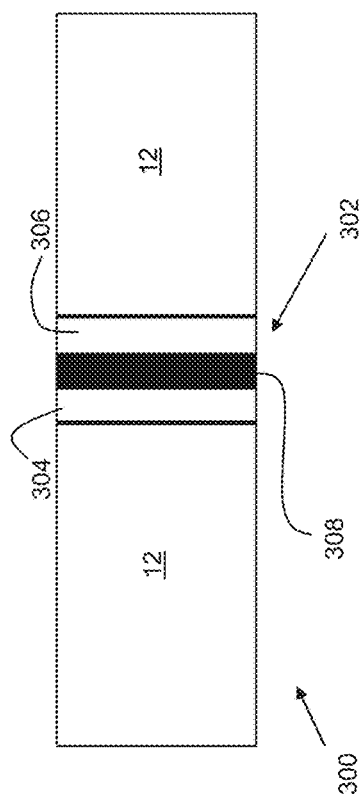
FIG. 48 illustrates another embodiment of an embolic device having a detachable joint.

FIG. 48 illustrates another embodiment of an embolic device 300 (e.g., a microcoil) having a plurality of electrolytic joints 102 that connect a plurality of coil segments 12, such that the device 300 can be selectively detached at a plurality of different locations. Specifically, the joint 302 preferably contains a proximal ring 304 and a distal ring 306 that are in contact with a middle sacrificial anode ring 308. A proximal end of a pusher (which is connected to a proximal end of the device 300) is connected to a power supply so as to provide positive current to the ring 304, while negative current is supplied via fluid from within the catheter 300 or through the patient's blood via an electrode in contact with the patient. The rings 304, 306 and the middle sacrificial anode ring 308 are selected so as to cause rapid galvanic corrosion of the anode ring 308 (i.e., the anode ring 308 acts as an anode and the rings 304, 306 act as a cathode). Once the anode ring 308 has sufficiently corroded, the distal coil portion 12 of the device 300 (including ring 106) disconnect from the proximal coil portion 12.

Figure 49:
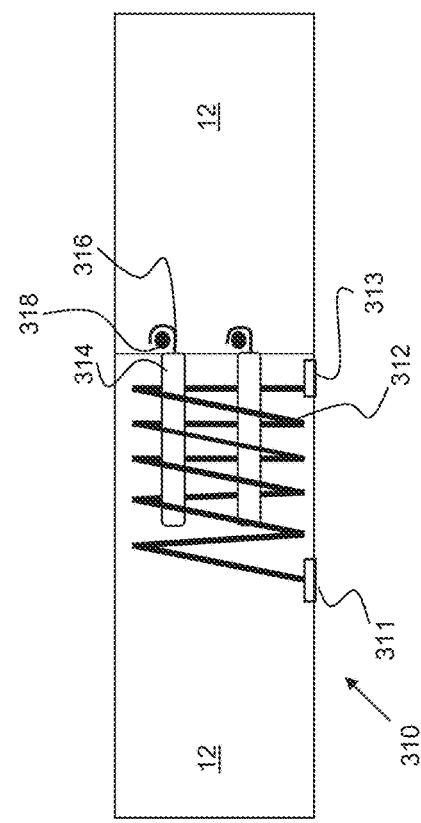
FIGS. 49-50 illustrate another embodiment of an embolic device having a detachable joint.
Figure 50:
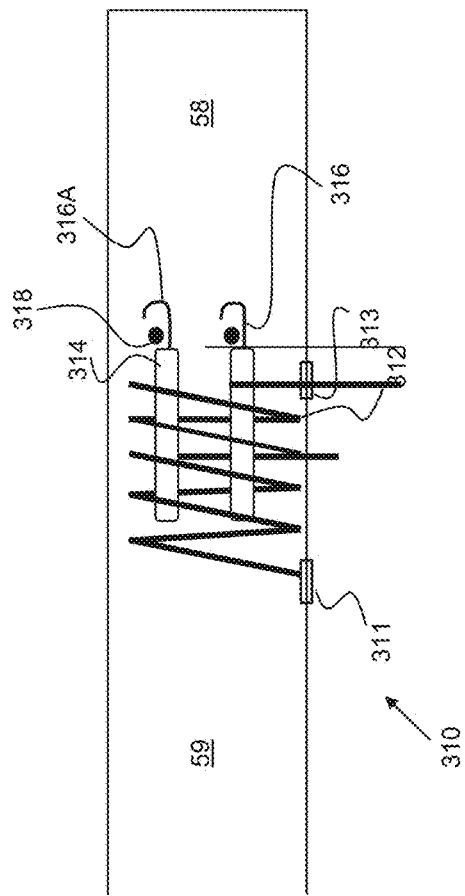
Figure 51:
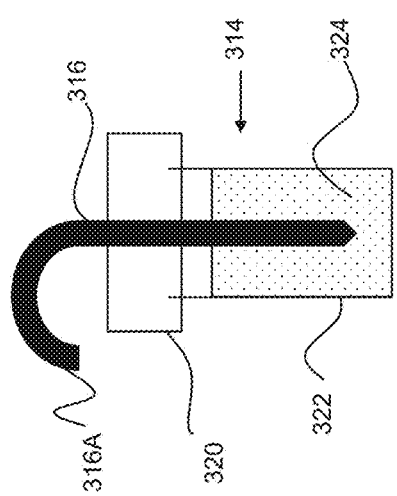
FIG. 51 illustrates a piston member of the detachment system of the catheter from FIGS. 49-50.

FIGS. 49-51 illustrate another embodiment of an embolic device 310 having a plurality of mechanical release mechanisms that can selectively detach and release the device 310 at various locations along the device 310. Specifically, the device 310 includes one or more pistons 314 having a pin 316 that moves outward to disengage the mechanical release mechanism. In one example, the mechanical release mechanism includes a hook portion 316A on the distal end of the pin 316 that can be moved from a latched position (FIG. 49) to an unlatched position (FIG. 50). However, it should be understood that a variety of different latching mechanisms can be used with the piston 314.

FIG. 19 illustrates one possible embodiment of the piston 314 in which a pressure-resistant housing 322 and cap 320 contain a material 324 that expands when heated. The material 324 can be any wax, oil, or similar material with a high enough coefficient of expansion to cause movement of the piston 314. In another example, the material 324 can be mercury, ethanol, or other materials with relatively high coefficients of expansion. When the heater coil 312 is activated, it heats up the pistons 314, causing the material 324 to expand within the housing 322, thereby pushing the pin 316 at least partially out of the housing 322.

Figure 52:
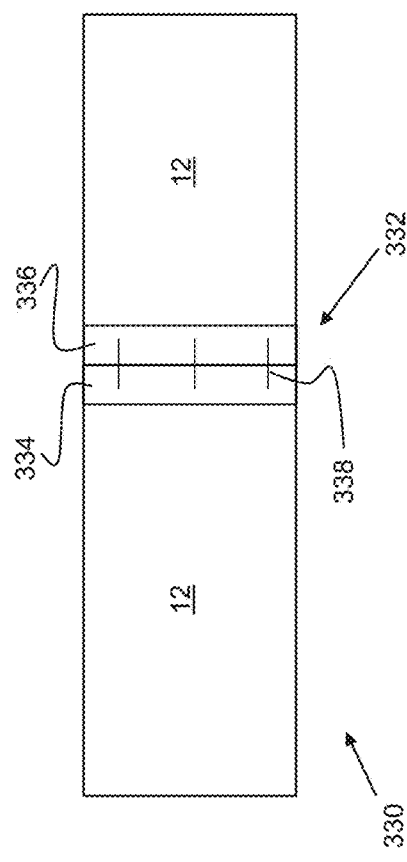
FIG. 52 illustrates another embodiment of an embolic device having a detachable joint.
Figure 54:
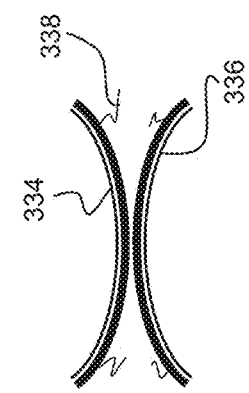
FIGS. 53-54 illustrate cross sectional views of the detachment system of FIG. 20.
Figure 53:
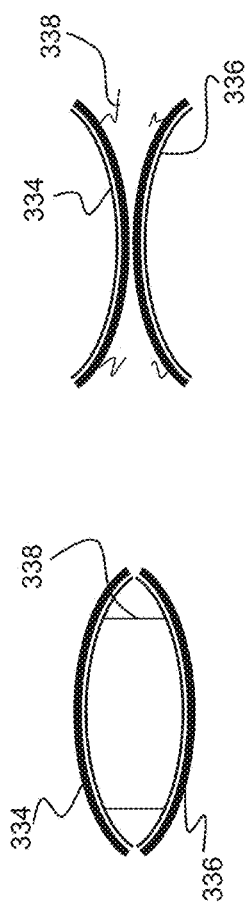
Figure 55:
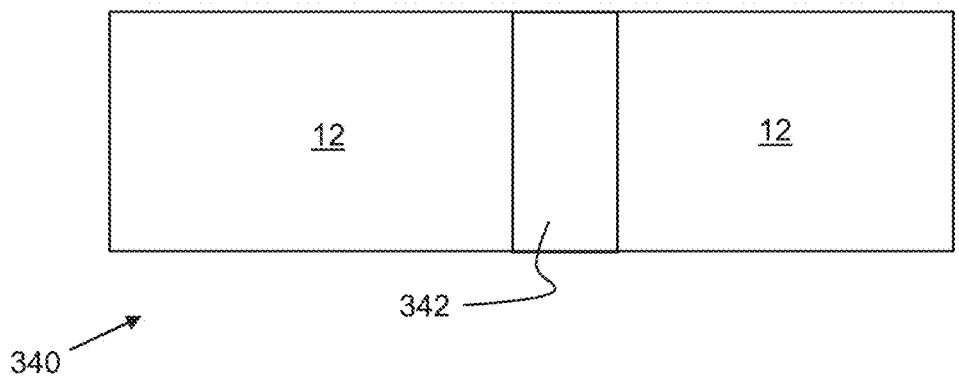
FIG. 55 illustrates another embodiment of an embolic device having a detachable joint.
Figure 56:
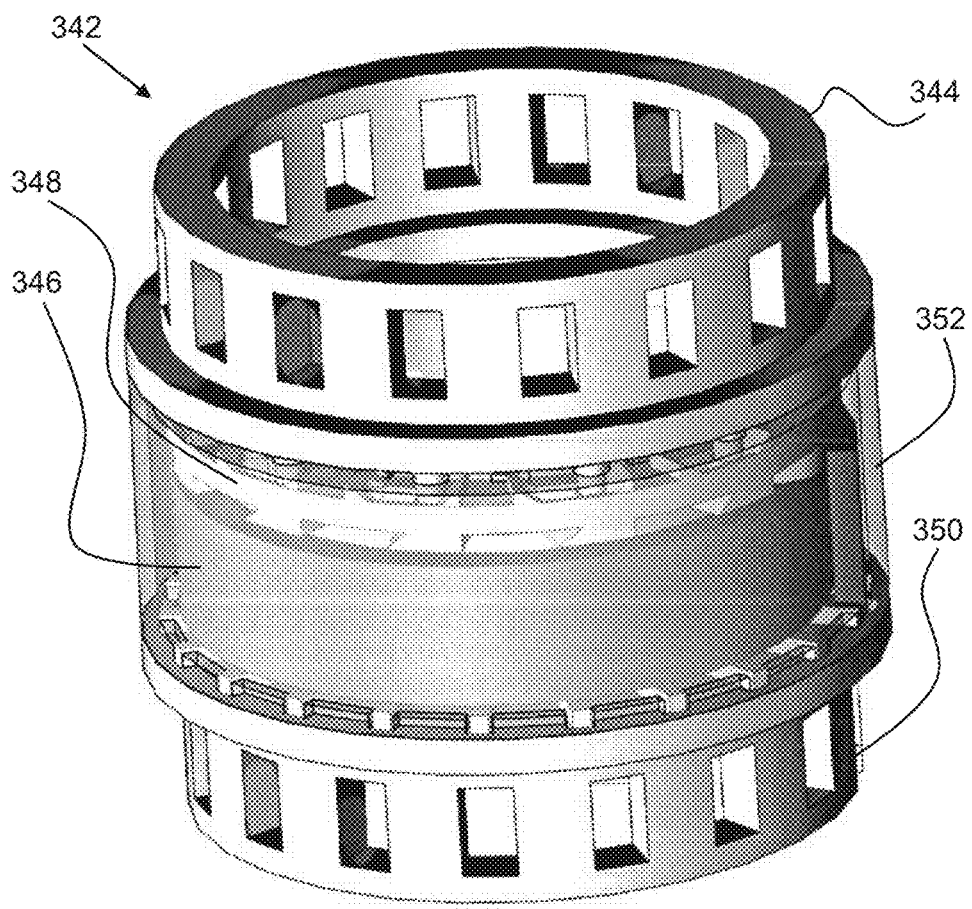
FIGS. 56-65 illustrate various components of the detachment system from the catheter of FIG. 55.
Figure 57:
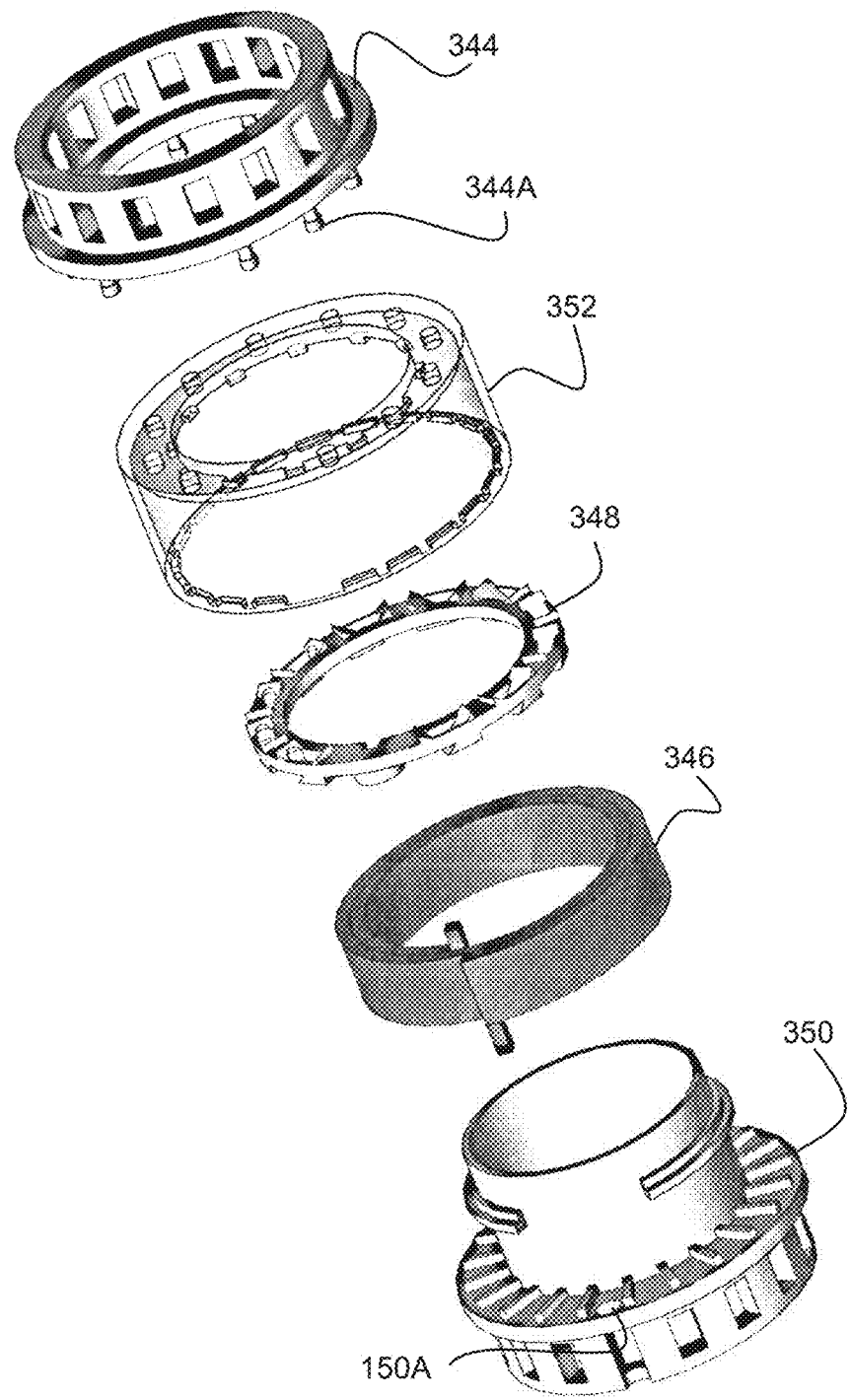
Figure 58:
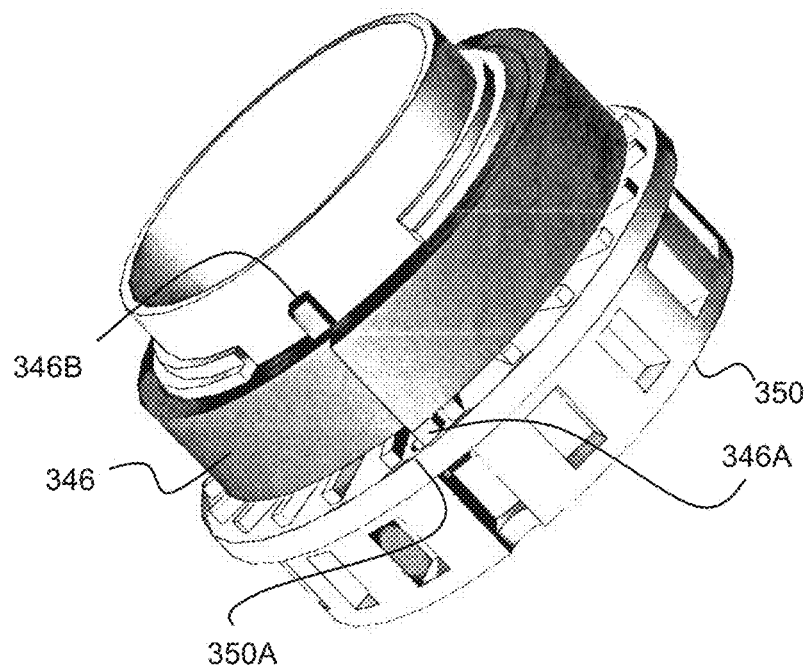
Figure 59:
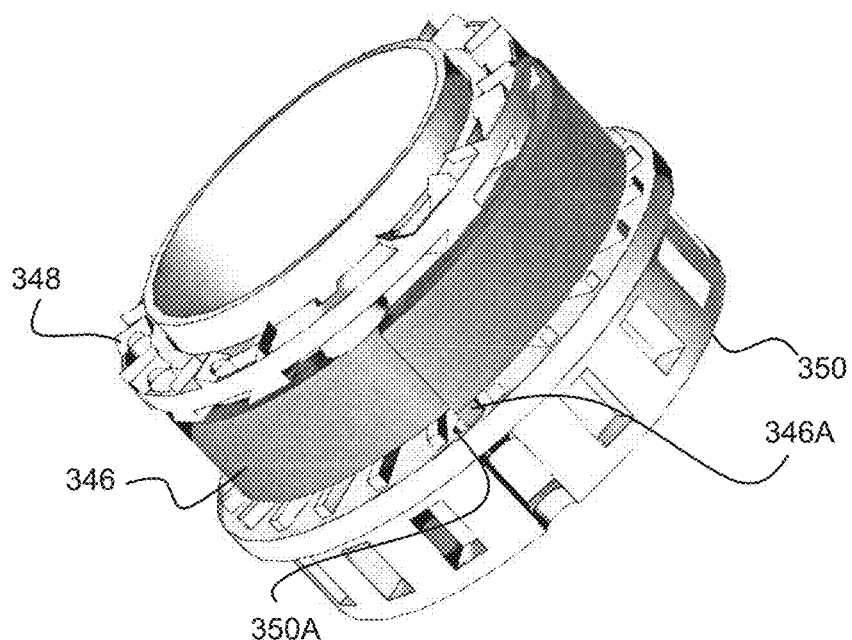
Figure 60:
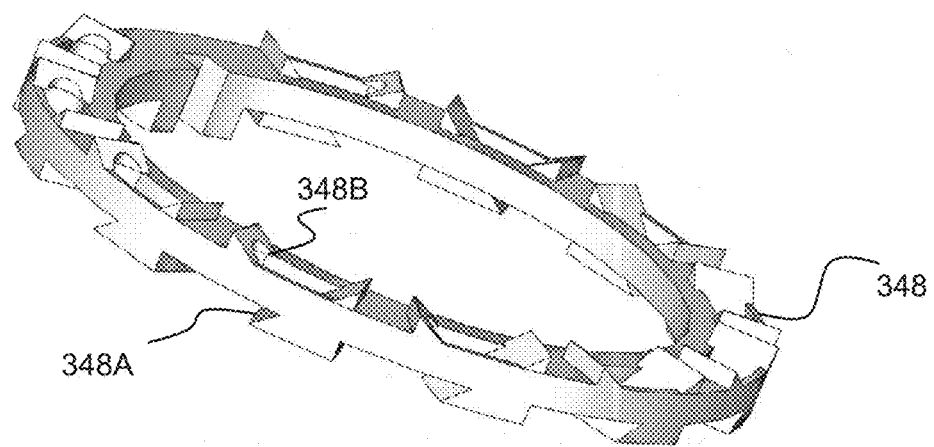

FIGS. 52-54 illustrate another embodiment of an embolic device 330 having a plurality of mechanical release mechanisms 332 connecting a plurality of coil segments 12. Specifically, the release mechanism 332 includes a proximal ring 334 and a distal ring 336 that are positioned against each other and are connected or held together via a plurality of tether members or filaments 338. As best seen in the cross sectional view of the ring in FIG. 53, the rings 334 and 336 initially have a generally concave shape relative to each other (e.g., forming a cross sectional oval between each other). However, when the rings 334 and 336 are heated, either by direct application of current to the rings (e.g., a previously described catheter) or by an adjacent heater coil in a catheter, the rings 334 and 336 bend in opposite directions to form convex shapes (FIG. 54). This shape change generally increases the distance of the ends of the rings from each other, where the tether members 338 are connected, thereby fracturing or breaking the tether members 338 and allowing the distal coil portion 12 of the device 330 to be disconnected from the proximal coil portion 12.

In one embodiment, the temperature bending behavior of the rings 334 and 336 can be created by using a bi-metal design (i.e., a first metal on a first side of the rings and a second, different metal on the second sides of the rings). In another embodiment, the bending behavior of the rings 334 and 336 can be created by using a material capable of Martensite/Austenite transitions. For example, the rings 334, 336 can be composed of Nitinol having a relatively high Austenite finish temperature, such that when current is applied to the rings or a heater coil is activated, the rings 334, 336 transition to their Austenite phase, thereby changing shape, as well.

FIGS. 55-65 illustrate another embodiment of an embolic device 340 (e.g., a microcoil) having a plurality of mechanical release mechanisms 342 that connect a plurality of coil portions 12 to each other. The mechanical release mechanism 342 preferably includes a heat-activated spring member 346 that maintains the mechanism 342 in a locked state during normal, operational temperatures (e.g., body temperature), but changes shape when heated, either by direct application of current or via an adjacent heater coil, to cause the mechanism 342 to unlock, thereby disconnecting adjacent coil portions 12 and releasing a portion of the embolic device 340 into the patient.

In one embodiment, the temperature bending behavior of the spring member 146 can be created by using a bi-metal design (i.e., a first metal on a first side of the spring member 346 and a second, different metal on the second side of the spring 346). In another embodiment, the shape-changing behavior of the spring member 346 can be created by using a material capable of Martensite/Austenite transitions. For example, the spring member 346 can be composed of Nitinol having a relatively high Austenite finish temperature, such that when current is applied to the spring or a heater coil is activated, the spring member 346 transitions to its Austenite phase, thereby changing shape, as well.

The spring member 346 of the mechanical release mechanism 342 is located on and around a base portion 350. The spring member 346 is further anchored in place on the base portion 350 by a first elongated anchor member 346A at one of its ends, extending into aperture 350A (best seen in FIG. 58). The spring member 346 also includes a second elongated anchor member 346B that extends into an aperture within the locking ring 348 (best seen in FIGS. 58 and 59). In this respect, the spring member 346 maintains the locking ring 348 in a first rotational position relative to the base portion 150 during normal operating temperatures (e.g., body temperature) and rotates the locking ring 348 when heated (via applied current or heater coil).

Figure 61:
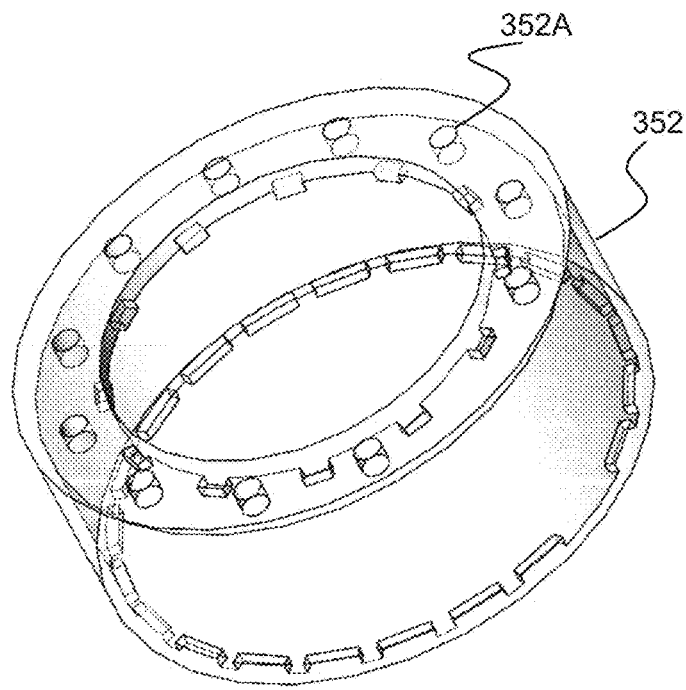
Figure 62:
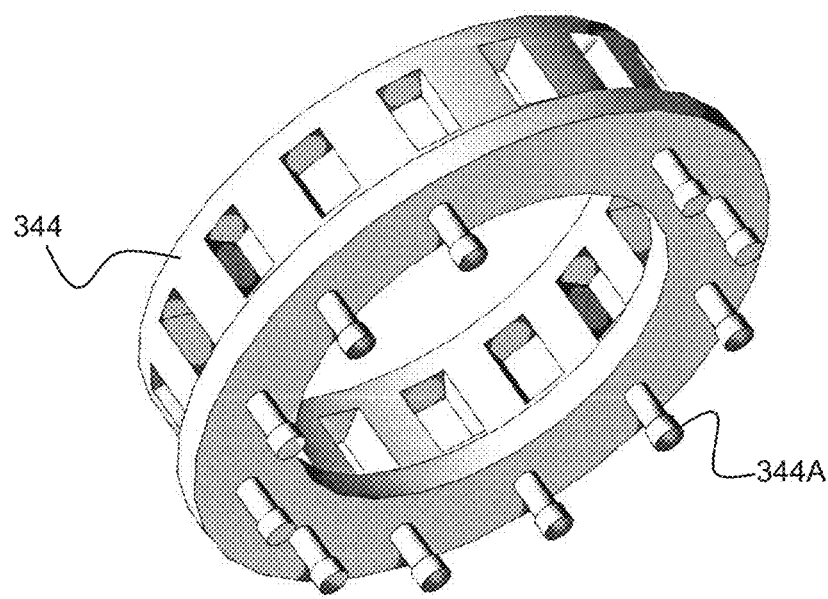

The base portion 350, spring member 346, and locking ring 348 are all preferably contained within an outer housing member 352, which helps maintain the axial positions of these members relative to each other. As best seen in FIG. 61, the outer housing member 352 includes a plurality of apertures 352A which allow passage of locking pins 344A on the ring 144.

Figure 63:
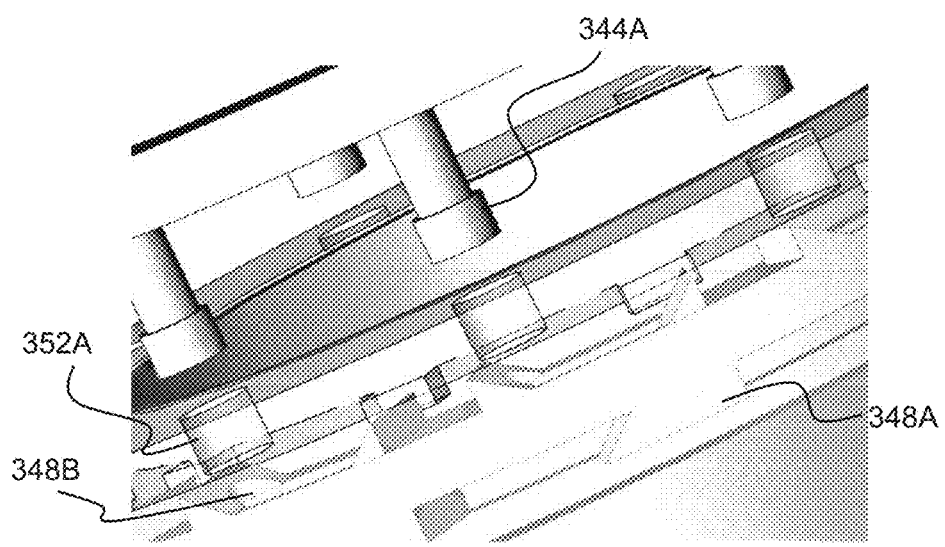
Figure 64:
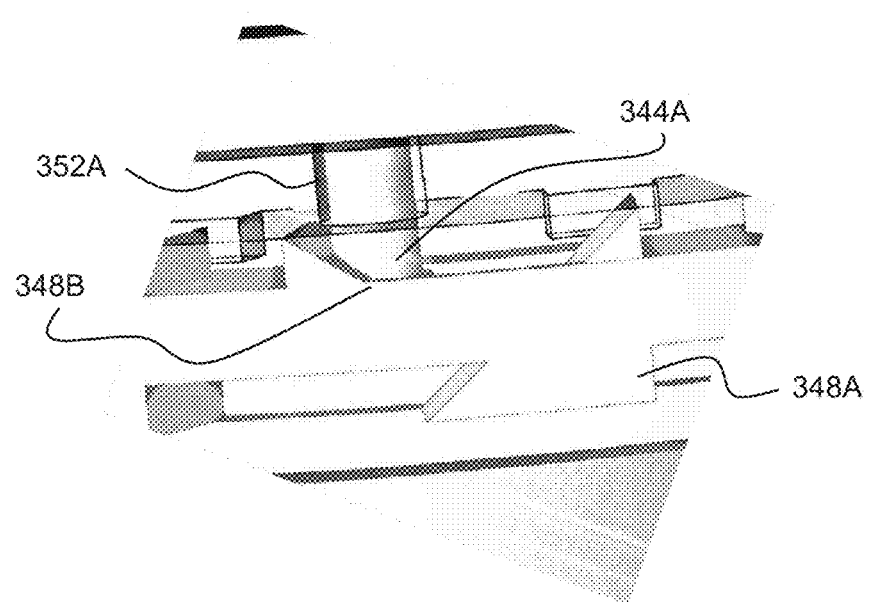
Figure 65:
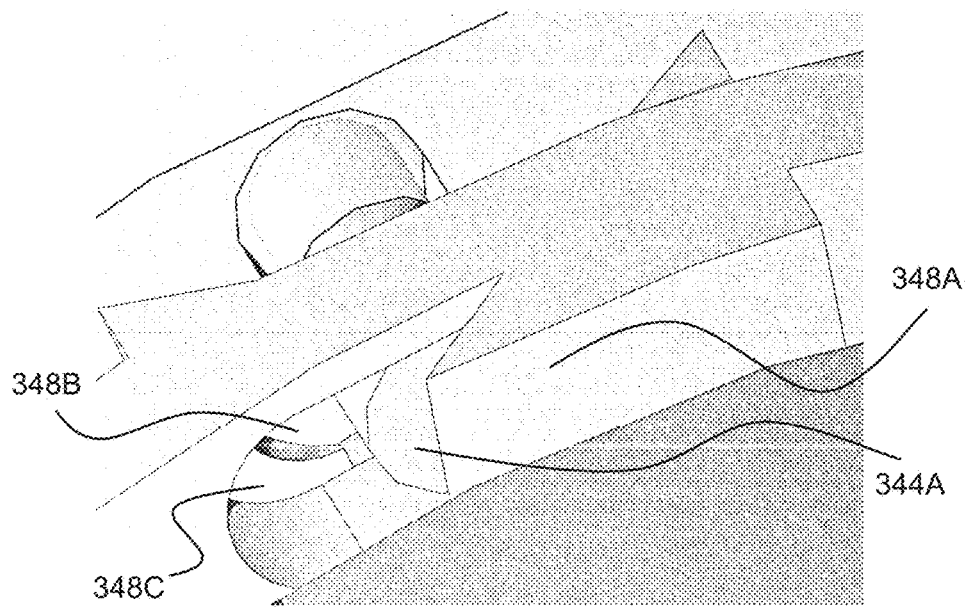

As best seen in FIGS. 63-65, the locking pins 344A pass through apertures 352A and into slots 348B on the locking ring 348. As best seen in FIG. 65, one end of each of the slots 348B include an overhanging portion or lip 348C that is sized and shaped to engage the distal ends of the pins 344A.

Specifically, the distal ends of the locking pins 344A have an enlarged diameter relative to the remaining, proximal portions, allowing this distal end to catch on the lip 348C and therefore prevent withdrawal of the pins 344A. Preferably, the spring member 346 is configured to maintain the locking ring 348 in a rotational position that maintains the lip 348C over distal end of the locking pins 344A.

At the opposite end of the slot 348B is a ramped surface 148A which assists in pushing the locking pins 344A out of the slot 348B. Specifically, the ramp 348A is inclined towards the ring 344, such that as the locking ring 348 rotates, the ramp 348A pushes the locking pins 344A axially outward of the housing 352. In this respect, when the spring member 346 is heated, the locking ring 348 rotates to disengage the locking pins 344A with the lip 348C and pushes the pins 344A outward. Since ring 344 and base portion 350 are each attached to either the proximal coil portion 12 or distal coil portion 12 of the device 340, unlocking the mechanism 342 separates the portions 12 from each other, detaching and releasing a portion of the device 340 from the remaining portion.

Alternately, rotation of the locking ring 344 of the mechanical release mechanism 342 can be performed via a different mechanism. For example, the previously described piston 314 could be fixed to the base 350 or housing 352, as well as the locking ring 344 so as to rotate the ring 344 when heat activates the piston 314.

Preferably, the locking ring 344 can be activated by locating the ring 344 near a heater coil of a catheter (as previously described) and activating the heater so as to cause detachment. Alternately, the catheter could provide current (e.g., see previously described catheter embodiments) to each side of the ring 344 when aligned with electrodes inside the catheter, causing the ring 344 to heat up when current is activated.

Figure 66:
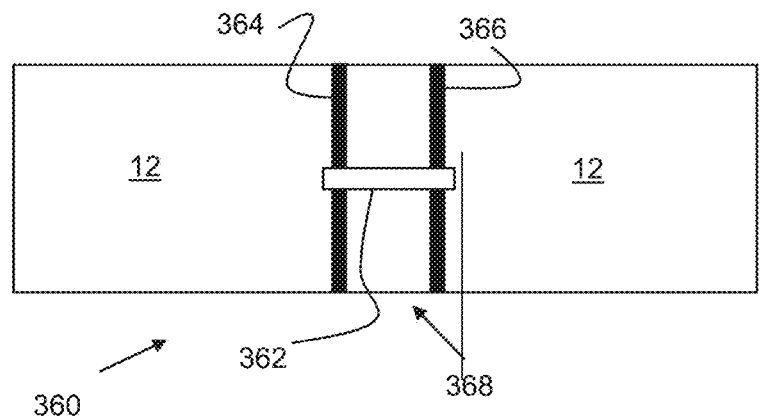
FIG. 66 illustrates another embodiment of an embolic device having a detachable joint.

FIG. 66 illustrates another embodiment of an embolic device 360 having a plurality of fuse release mechanisms 142 that releasably connect a plurality of coil segments 12. Specifically, the coil portions 12 can be held together by one or more (e.g., a plurality) of fuse members 362 located near the circumference of the catheter 360.

The fuse members 362 are preferably connected to a proximal ring 364 and a distal ring 366. The proximal ring 364 is connected to the distal ring 366 via the fuse members 362. Preferably, the fuse member 162 is composed of a material that can be fractured or broken without causing enough heat to damage surrounding tissue in a patient (this breaking value is sometimes referred to as the "clearing I2t" value). In one example, the fuse can be composed of an elongated hypotube of gold plated polyimide material.

When the rings 364 and 366 are aligned with electrodes within a catheter (e.g., see previous catheter embodiments) and current is activated, the current passes through effuse members 362, thereby fracturing the members 362 and releasing a portion of the device 360.

Figure 67:
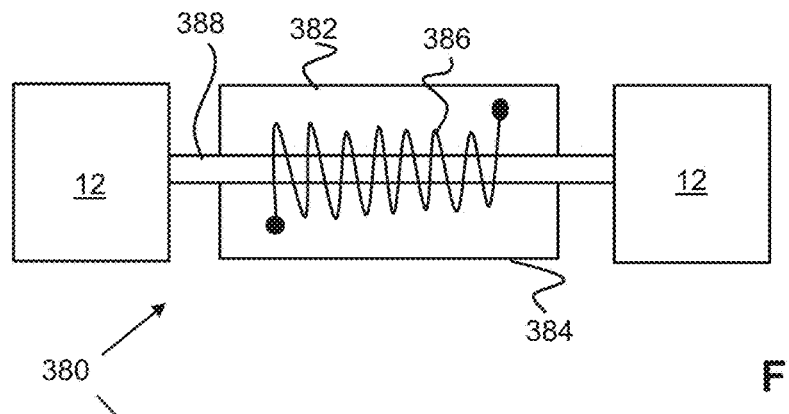
FIGS. 67-68 illustrate another embodiment of an embolic device having a detachable joint.
Figure 68:
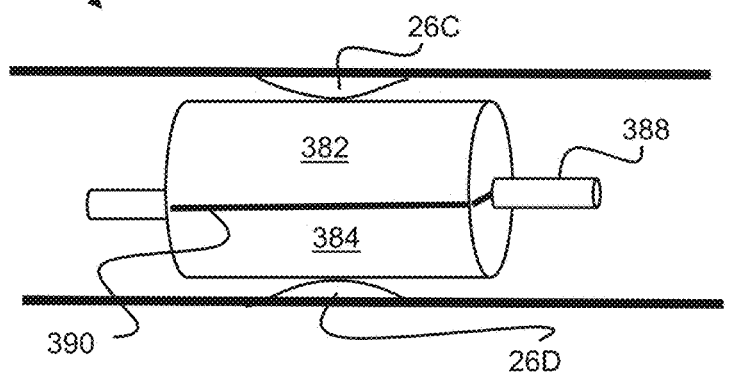

FIGS. 67 and 68 illustrate another embodiment of a releasable joint 380 for an embolic device having a plurality of coil segments 12. Adjacent coil segments 12 are maintained together via a monofilament or tether member 388 (e.g., via tying or via adhesives at each end of the tether 388). As seen best in FIG. 67, a heating coil 386 is located around the tether 384. A first end of the heating coil 386 is connected to a first conductive housing member 382 while a second end of the heating coil 386 is connected to a second conductive housing member 384. When the housing members 382 and 384 are aligned with positive electrode 26C and negative electrode 26D (e.g., each housing member is contacting a different electrode), current passes through the heating coil 386, generating heat, and breaking or melting the tether 388 to release the portion of the device distal of the joint 380. To prevent the housing from shorting out the electrical system, an insulating layer 390 is disposed between the two housing members 382 and 384. In one embodiment, the embolic device and catheter may be keyed or otherwise shaped to maintain a desired rotational orientation so that the housing members 382, 384 properly align with electrical contacts 26C and 26D.

The embodiment of FIGS. 67-68 could also be used in the capsule system of FIGS. 11-12, that is the joint 380 could utilize a spring at both ends of the joint or one spring spanning the entirety of the joint. Monofilament 388 would either be tied to both springs, or tied to two ends of one spring as shown in FIG. 12. When heat is generated, the spring would expand causing the monofilament to break, similar to the embodiments of FIGS. 11-12.

FIGS. 69 (exploded view) and 70 (assembled view) illustrate another embodiment of a releasable joint 400 for an embolic device having a plurality of coil segments. Specifically, the proximal coil segment 402 is releasably connected to the distal coil segment 406 by an intermediate coil segment 404 and a fuse release mechanism 408. The fuse release mechanism 408 includes a proximal capsule member 416 that includes a fuse member 414 and a distal capsule member 410 which includes a fixed loop 412 through which the fuse member 414 passes through to interlock the capsule members 410 and 416 together.

Preferably, the capsule members 410 and 416 are composed of a material that tolerates relatively high temperatures but does not conduct electricity, such as ceramic. The proximal capsule member 416 preferably has a conductive element 416A (e.g., platinum) insert molded into the member 416, serving as a connection point for the end of the fuse member 414 and as a connection point to the intermediate coil 404 (e.g., by welding). The proximal capsule member 416 is preferably welded near the distal end of the intermediate coil 404 so as to make an electrical connection with the coil 404. Similarly, the distal capsule member 410 includes metal elements 410A and loop 412 press molded into it, allowing the metal elements 410A to be welded to the inside of the distal coil segment 406.

The proximal coil segment 402 preferably includes an insulated portion 402A along its distal portion, such as a ceramic based or titanium based coating. Similarly, the intermediate coil segment 404 includes an insulated portion 404A along its proximal portion. In an assembled state (e.g., FIG. 70), only the insulated portions 402A and 404A are intertwined with each other, so that the proximal segment 402 and the intermediate segment 404 become mechanically connected to each other, but not electrically connected. Finally, a fuse link 418 is connected to the fuse 414 and to the uninsulated portion of the proximal segment 402 (e.g., via welding at location 418A).

In operation, the embolic coil is advanced within a catheter, such as any of the catheters described in this specification (e.g., the catheter of FIG. 4). The uninsulated portion of the intermediate segment 404 is aligned with a first electrical contact 26A within the catheter 22 and the uninsulated portion of the proximal segment 402 is aligned with a second electrical contact 26B. At this time, a circuit is completed through the second electrical contact 26B, the fuse link 418, into the fuse 414, through conductive element 416A, into the intermediate coil segment 404, and finally into the first electrical contact 26A. A power supply and interface device can sense alignment via completion of the circuit (e.g., via application of a low level of current). When the user wishes to detach the distal segment 406, a high level of current is applied from the power supply and interface device, causing the fuse 414 to break, thereby releasing the distal capsule member 410 and the distal coil segment 406. Since the fuse 414 is broken, the interface and power supply can detect a break in the circuit and can thereby confirm that detachment has occurred.

Preferably, the components of the releasable joint 400 are all composed of material that can withstand about 700 degrees Celsius for 45 minutes (e.g., insulating ceramic materials and titanium based coatings). This allows an entire embolic device to be created with one or more of the releasable joints 400, then heat set into secondary shapes without damaging the components of the joints 400. Additionally, since the non-coil components are located within the coil segments, there may be less friction or ratcheting between the joints and the catheter and/or catheter's electrical contacts.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An embolic coil delivery system comprising:
a catheter including a first contact and a second contact;
an embolic coil including two segments separated by a link; the link including a proximal conductive sleeve, a distal conductive sleeve, and a monofilament between the proximal and the distal conductive sleeves;
wherein a circuit is completed when the catheter's first and second contacts are aligned in electrical communication with the link's proximal and distal conductive sleeves, and wherein the monofilament is degradable in response to the circuit being completed such that the two segments of the embolic coil detach from each other in response to the monofilament degrading.

2. The embolic coil delivery system of claim 1, wherein the first contact and second contact have opposing polarities.

3. The embolic coil delivery system of claim 1, wherein the link includes a heater.

4. The embolic coil delivery system of claim 3, wherein the heater is a heater coil.

5. The embolic coil delivery system of claim 3, wherein the monofilament passes through the heater.

6. The embolic coil delivery system of claim 3, where a spring is disposed over the monofilament.

7. The embolic coil delivery system of claim 1, further comprising a user interface, wherein a video or audio cue is produced from the user interface when the first contact and the second contact of the catheter are aligned with the proximal conductive sleeve and the distal conductive sleeve of the link.

8. The embolic coil delivery system of claim 1, further comprising a user interface wherein a button of the user interface, once actuated, initiates a detachment sequence to cause the two segments of the embolic coil to detach from each other.

9. The embolic coil delivery system of claim 1, wherein the link includes an insulating sleeve between the proximal and distal conductive sleeves.

10. An embolic coil delivery system comprising:
a catheter comprising an interior passage;
a distal electrical contact and a proximal electrical contact that are both located within the interior passage of the catheter and near a distal end of the catheter; the distal electrical contact and the proximal electrical contact being in electrical communication with a proximal end of the catheter;
an embolic coil comprising a first coil segment and a second coil segment;
a coil link connected between the first coil segment and the second coil segment; the coil link comprising:
  a first coil electrical contact exposed on an outer surface of the coil link;
  a second coil electrical contact exposed on an outer surface of the coil link;
  a heater connected to the first coil electrical contact and the second coil electrical contact; and,
  a filament fixed to a distal portion of the coil link and to a proximal portion of said coil link;
wherein the first coil electrical contact and the second coil electrical contact are spaced apart so as to contact the distal electrical contact and the proximal electrical contact, respectively, simultaneously; and
wherein applying current through the first coil electrical contact, the distal electrical contact, the second coil electrical contact, and the proximal electrical contact increases the temperature of the heater to break the filament and thereby sever the coil link.

11. The embolic coil delivery system of claim 10, wherein the heater is a heater coil.

12. The embolic coil delivery system of claim 11, wherein the heater coil is located within an insulating sleeve.

13. The embolic coil delivery system of claim 10, further comprising a first spring located on a distal end of the coil link and a second spring located on a proximal end of the coil link.

14. The embolic coil delivery system of claim 13, wherein the first spring tapers in a distal direction and the second spring tapers in a proximal direction.

15. The embolic coil delivery system of claim 13, wherein the filament is fixed to the first spring and to the second spring.

16. The embolic coil delivery system of claim 15, wherein the filament is in tension between the first spring and the second spring.

17. The embolic coil delivery system of claim 10, wherein the first coil electrical contact and the second coil electrical contact are both cylindrical sleeves.

18. The embolic coil delivery system of claim 10, further comprising a user interface connected to the delivery system that creates a signal when the first coil electrical contact and the second coil electrical contact are respectively aligned and contacting the distal electrical contact and the proximal electrical contact.

* * * * *